US010062244B2

(12) United States Patent
You et al.

(10) Patent No.: US 10,062,244 B2
(45) Date of Patent: Aug. 28, 2018

(54) METHOD AND APPARATUS FOR ASSOCIATING DATA WITH TIME INFORMATION

(71) Applicant: Samsung Electronics Co., Ltd, Gyeonggi-do (KR)

(72) Inventors: Sang-Hoon You, Seoul (KR); Jong-Jin Kim, Gyeonggi-do (KR); Jong-Hwan Kim, Gyeonggi-do (KR); Chan-Hyoung Park, Gyeonggi-do (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/393,208

(22) Filed: Dec. 28, 2016

(65) Prior Publication Data
US 2017/0243448 A1 Aug. 24, 2017

(30) Foreign Application Priority Data
Feb. 18, 2016 (KR) .......................... 10-2016-0019326

(51) Int. Cl.
| | | |
|---|---|---|
| G08B 23/00 | (2006.01) | |
| G08B 1/08 | (2006.01) | |
| G06F 17/30 | (2006.01) | |
| H04L 12/26 | (2006.01) | |
| H04L 12/00 | (2006.01) | |
| G16H 40/63 | (2018.01) | |

(52) U.S. Cl.
CPC ......... *G08B 1/08* (2013.01); *G06F 17/30619* (2013.01); *G16H 40/63* (2018.01); *H04L 12/00* (2013.01); *H04L 43/08* (2013.01)

(58) Field of Classification Search
CPC .... G01D 9/005; G06F 3/017; A61B 256/0242
USPC ........................................................ 340/517
See application file for complete search history.

(56) References Cited

U.S. PATENT DOCUMENTS

| | | | | |
|---|---|---|---|---|
| 2002/0171741 | A1* | 11/2002 | Tonkin ................... | H04N 7/181 348/211.3 |
| 2012/0254878 | A1* | 10/2012 | Nachman .............. | G06F 9/5094 718/102 |
| 2015/0185054 | A1* | 7/2015 | Hesch .................... | G01D 9/005 702/187 |
| 2015/0317230 | A1* | 11/2015 | Le Grand .............. | G01D 9/005 702/187 |
| 2016/0173606 | A1* | 6/2016 | Noda ...................... | G06F 9/445 709/217 |

\* cited by examiner

*Primary Examiner* — Fabricio R Murillo Garcia

(57) ABSTRACT

An electronic device including a sensor, a first processor, and a second processor and a method for associating data with time information are provided. The method includes including receiving a notification signal corresponding to the data from the first processor, determining time information and first identification information that correspond to the notification signal in response to the reception, receiving the data and second identification information corresponding to the notification signal from the first processor, associating the data with the time information at least based on the first identification information and the second identification information, and providing the data associated with the time information to an application. Other various embodiments may also be possible.

16 Claims, 13 Drawing Sheets

METHOD AND APPARATUS FOR ASSOCIATING DATA WITH TIME INFORMATION

CROSS-REFERENCE TO RELATED APPLICATION(S) AND CLAIM OF PRIORITY

The present application is related to and claims the benefit under 35 U.S.C. § 119(a) of a Korean patent application filed in the Korean Intellectual Property Office on Feb. 18, 2016 and assigned Serial No. 10-2016-0019326, the entire disclosure of which is incorporated herein by reference.

TECHNICAL FIELD

Various embodiments of the present disclosure relate to a method and apparatus for associating data with time information related to the data, for example, a method and apparatus for associating data sensed by a sensor with time information.

BACKGROUND

An electronic device may include a plurality of processors. The electronic device may include a main processor (e.g., an application processor) and a low-energy processor (e.g., a low power processor), and the low-energy processor consumes a less amount of current than the main processor and processes sensor data with low power to recognize a surrounding situation. The electronic device provides information (e.g., pedometer, etc.) meaningful to a user by using sensor data, and also provides a new function by combining the sensor data with another data (e.g., an image, etc.).

The electronic device is capable of receiving sensor data from at least one sensor through a first processor (e.g., a low power processor), which then processes the received sensor data, associates the processed sensor data with time information, and delivers the sensor data to a second processor (a main processor). However, due to a difference between a point in time when the sensor data is generated and a point in time when the time information related to the sensor data is generated, the time information of the sensor data may not be accurate. Moreover, the second processor and the first processor generate their time information by using different time sources, even data generated at the same point in time may not be temporally synchronized.

The above information is presented as background information only to assist with an understanding of the present disclosure. No determination has been made, and no assertion is made, as to whether any of the above might be applicable as prior art with regard to the present disclosure.

SUMMARY

To address the above-discussed deficiencies, it is a primary object to provide a first processor, upon receiving sensor data, sends a notification signal to a second processor, which then obtains time information corresponding to the notification signal and associates the obtained time information with the sensor data received from the first processor.

According to various embodiments of the present disclosure, there is provided an electronic device including a sensor, a first processor capable of obtaining data sensed using the sensor, and a second processor capable of executing an application, in which the second processor is configured to receive a notification signal corresponding to the data from the first processor, to determine time information and first identification information that correspond to the notification signal in response to the reception, to receive the data and second identification information corresponding to the notification signal from the first processor, to associate the data with the time information at least based on the first identification information and the second identification information, and to provide the data associated with the time information to the application.

According to various embodiments of the present disclosure, there is provided an electronic device including a sensor, a first processor capable of obtaining data sensed using the sensor, and a second processor capable of executing an application, in which the first processor is configured to send a notification signal corresponding to the data to the second processor, to determine identification information corresponding to the data, and to transmit the data and identification information corresponding to the data to the second processor.

According to various embodiments of the present disclosure, there is provided, in an electronic device including a sensor, a first processor, and a second processor, a method for associating data with time information including receiving a notification signal corresponding to data sensed using the sensor from the first processor, determining time information and first identification information that correspond to the notification signal by using the second processor in response to the reception, receiving the data and second identification information corresponding to the notification signal from the first processor, associating the data with the time information at least based on the first identification information and the second identification information, and providing the data associated with the time information to an application by using the second processor.

According to various embodiments of the present disclosure, there is provided, in an electronic device including a sensor, a first processor, and a second processor, a method for associating data with time information including sending a notification signal corresponding to data sensed using the sensor to the second processor by using the first processor, determining identification information corresponding to the data by using the first processor, and transmitting the data and the identification information corresponding to the data to the second processor by using the first processor.

Other aspects, advantages, and salient features of the disclosure will become apparent to those skilled in the art from the following detailed description, which, taken in conjunction with the annexed drawings, discloses exemplary embodiments of the disclosure.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

Throughout the drawings, like reference numerals will be understood to refer to like parts, components, and structures.

DETAILED DESCRIPTION

Figure 1:
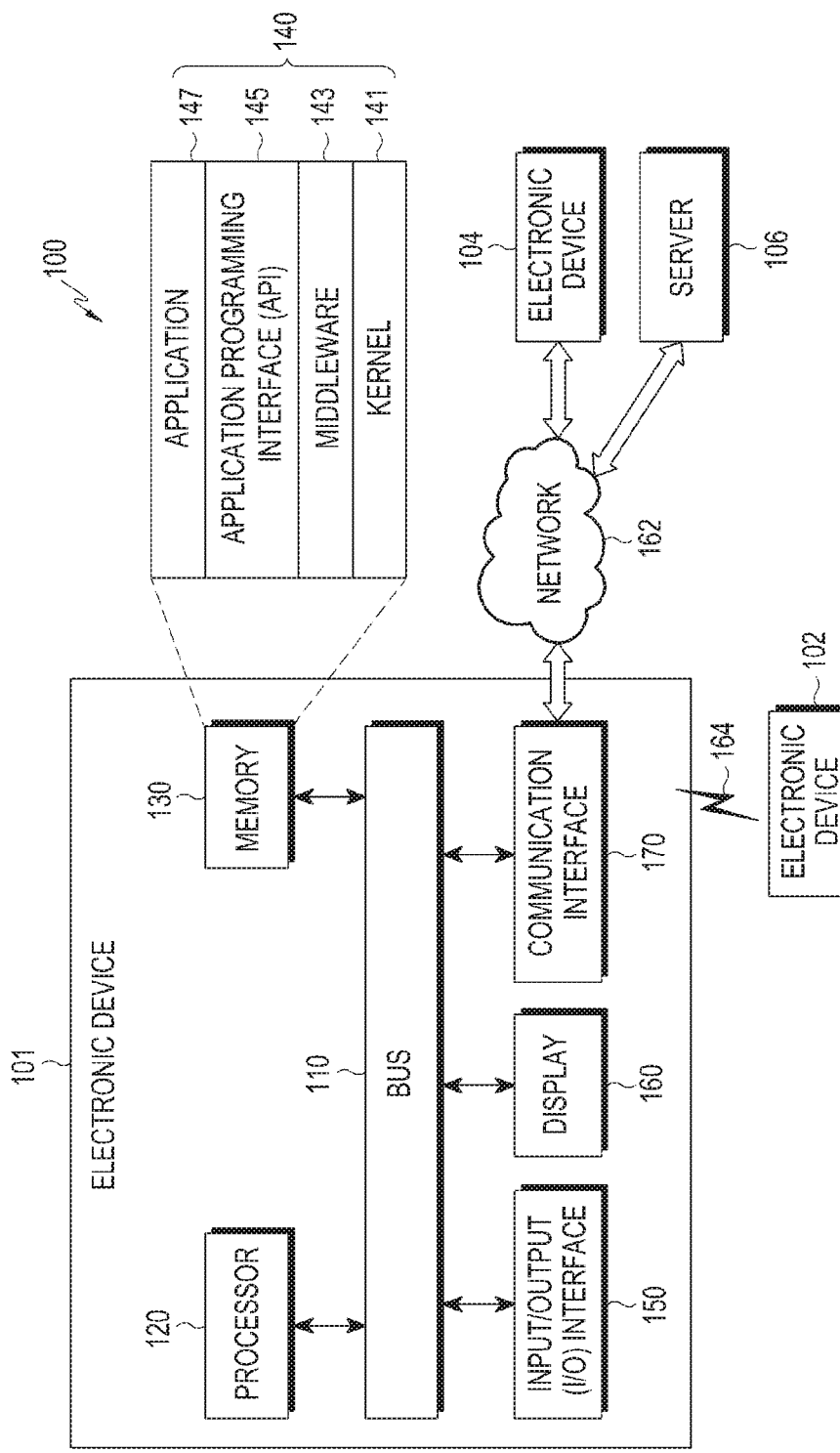
FIG. 1 illustrates an example of a network environment according to various embodiments of the present disclosure.

FIGS. 1 through 11, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged electronic device.

Hereinafter, various embodiments of the present disclosure will be disclosed with reference to the accompanying drawings. However, the description is not intended to limit the present disclosure to particular embodiments, and it should be construed as including various modifications, equivalents, and/or alternatives according to the embodiments of the present disclosure. In regard to the description of the drawings, like reference numerals refer to like elements.

In the present disclosure, an expression such as "having," "may have," "comprising," or "may comprise" indicates existence of a corresponding characteristic (e.g., a numerical value, a function, an operation, or an element like a part) and does not exclude existence of additional characteristic.

In the present disclosure, an expression such as "A or B," "at least one of A or/and B," or "one or more of A or/and B" may include all possible combinations of together listed items. For example, "A or B," "at least one of A and B," or "one or more of A or B" may indicate the entire of (1) including at least one A, (2) including at least one B, or (3) including both at least one A and at least one B.

Expressions such as "first," "second," "primarily," or "secondary," used herein may represent various elements regardless of order and/or importance and do not limit corresponding elements. For example, a first user device and a second user device may represent different user devices regardless of order or importance. For example, a first element may be named as a second element without departing from the right scope of the various exemplary embodiments of the present disclosure, and similarly, a second element may be named as a first element.

When it is described that an element (such as a first element) is "operatively or communicatively coupled with/to" or "connected" to another element (such as a second element), the element can be directly connected to the other element or can be connected to the other element through another element (e.g., a third element). However, when it is described that an element (such as a first element) is "directly connected" or "directly coupled" to another element (such as a second element), it means that there is no intermediate element (such as a third element) between the element and the other element.

An expression "configured to (or set)" used in the present disclosure may be replaced with, for example, "suitable for," "having the capacity to," "designed to," "adapted to," "made to," or "capable of" according to a situation. A term "configured to (or set)" does not always mean only "specifically designed to" by hardware. Alternatively, in some situation, an expression "apparatus configured to" may mean that the apparatus "can" operate together with another apparatus or component. For example, a phrase "a processor configured (or set) to perform A, B, and C" may be a dedicated processor (e.g., an embedded processor) for performing a corresponding operation.

or a generic-purpose processor (such as a CPU or an application processor) that can perform a corresponding operation by executing at least one software program stored at a memory device.

Terms defined in the present disclosure are used for only describing a specific exemplary embodiment and may not have an intention to limit the scope of other exemplary embodiments. The singular forms are intended to include the plural forms as well, unless the context clearly indicates otherwise. All of the terms used herein including technical or scientific terms have the same meanings as those generally understood by an ordinary skilled person in the related art. The terms defined in a generally used dictionary should be interpreted as having meanings that are the same as or similar with the contextual meanings of the relevant technology and should not be interpreted as having ideal or exaggerated meanings unless they are clearly defined in the various exemplary embodiments. In some case, terms defined in the present disclosure cannot be analyzed to exclude the present exemplary embodiments.

An electronic device according to various embodiments of the present disclosure may include at least one of, for example, a smartphone, a tablet personal computer (PC), a mobile phone, a video phone, an electronic-book (e-book) reader, a desktop PC, a laptop PC, a netbook computer, a workstation, a server, a personal digital assistant (PDA), a portable multimedia player (PMP), an MP3 player, a mobile medical equipment, a camera, and a wearable device. According to various embodiments, examples of the wearable device may include at least one of an accessory type (e.g., a watch, a ring, a bracelet, an anklet, a necklace, glasses, contact lenses, head-mounted device (HMD), etc.), a fabric or cloth-integrated type (e.g., electronic clothing, etc.), a body-attached type (e.g., a skin pad, a tattoo, etc.), a body implanted type (e.g., an implantable circuit, etc.), and so forth.

According to various embodiments of the present disclosure, an electronic device may be a home appliance. The home appliance may include, for example, a television (TV), a digital video disk (DVD) player, audio equipment, a refrigerator, an air conditioner, a vacuum cleaner, an oven, a microwave oven, a laundry machine, an air cleaner, a set-top box, a home automation control panel, a security control panel, a TV box (e.g., HomeSync™ of Samsung, TV™ of Apple, or TV™ of Google), a game console, an electronic dictionary, an electronic key, a camcorder, and an electronic frame.

According to various embodiments of the present disclosure, the electronic device may include at least one of various medical equipment (for example, magnetic resonance angiography (MRA), magnetic resonance imaging (MRI), computed tomography (CT), an imaging device, or an ultrasonic device), a navigation system, a global positioning system (GPS) receiver, an event data recorder (EDR), a flight data recorder (FDR), a vehicle infotainment device, electronic equipment for ships (e.g., a navigation system and gyro compass for ships), avionics, a security device, a vehicle head unit, an industrial or home robot, an automatic teller's machine (ATM), a Point of Sales (POS), Internet of things (e.g., electric bulbs, various sensors, electricity or gas meters, sprinkler devices, fire alarm devices, thermostats, streetlights, toasters, exercise machines, hot-water tanks, heaters, boilers, and so forth).

According to some embodiments, the electronic device may include a part of furniture or building/structure, an electronic board, an electronic signature receiving device, a projector, and various measuring instruments (e.g., a water, electricity, gas, electric wave measuring device, etc.). The electronic device according to various embodiments of the present disclosure may be one of the above-listed devices or a combination thereof. The electronic device according to some embodiments may be a flexible electronic device. The electronic device according to various embodiments of the present disclosure is not limited to the above-listed devices and may include new electronic devices according to technical development.

According to various embodiments of the present disclosure, a notification signal (e.g., an interrupt signal) may include data for instructing a processor to execute an operation of obtaining time information (e.g., a timestamp) in order of high priority to low priority. For example, a processor having received the interrupt signal may obtain time information corresponding to a point in time when the signal is received.

According to various embodiments of the present disclosure, an index is identification information necessary for associating sensor data with time information, and may increase based on sending of a notification signal from a first processor to a second processor when the first processor receives sensor data from at least one sensor. The index may increase based on the notification signal both in the first processor and the second processor. The index may be included in the sensor data and the time information.

According to various embodiments of the present disclosure, the time information may include a timestamp value as information indicating a particular point in time.

Hereinafter, a description will be made of a method and apparatus for associating data with time information between processors according to various embodiments of the present disclosure with reference to the accompanying drawings. Herein, the term "user" used in various embodiments of the present disclosure may refer to a person who uses the electronic device or a device using the electronic device.

FIG. 1 illustrates an example of a network environment according to various embodiments of the present disclosure.

Referring to FIG. 1, a network environment 100 may include an electronic device 101, at least one electronic device (e.g., a first electronic device 102 or a second electronic device 104), and a server 106, and each of the elements may be connected over a network 162 or to the electronic device 101 through a communication interface 170 of the electronic device 101.

The electronic device 101 may include a bus 110, a processor 120, a memory 130, an input/output (I/O) interface 150, a display 160, and a communication interface 170. According to some embodiments, the electronic device 101 may omit at least one of the foregoing elements or may further include other elements.

The bus 110 may include a circuit for connecting, e.g., the elements 110 to 170 and delivering communication (e.g., a control message and/or data) between the elements 110 to 170.

The processor 120 may include one or more of a central processing unit (CPU), an application processor (AP), and a communication processor (CP). The processor 120 performs operations or data processing for control and/or communication of, for example, at least one other elements of the electronic device 101.

The memory 130 may include a volatile and/or nonvolatile memory. The memory 130 may store, for example, commands or data associated with at least one other elements of the electronic device 101. According to an embodiment of the present disclosure, the memory 130 may store software and/or a program 140. The program 140 may include at least one of, for example, a kernel 141, middleware 143, an application programming interface (API) 145, and/or an application program (or "application") 147, and the like. At least some of the kernel 141, the middleware 143, and the API 145 may be referred to as an operating system (OS).

The kernel 141 may control or manage, for example, system resources (e.g., the bus 110, the processor 120, the memory 130, etc.) used to execute operations or functions implemented in other programs (e.g., the middleware 143, the API 145, or the application program 147). The kernel 141 provides an interface through which the middleware 143, the API 145, or the application program 147 accesses separate components of the electronic device 101 to control or manage the system resources.

The middleware 143 may work as an intermediary for allowing, for example, the API 145 or the application program 147 to exchange data in communication with the kernel 141.

In addition, the middleware 143 may process one or more task requests received from the application program 147 based on priorities. For example, the middleware 143 may give a priority for using a system resource (e.g., the bus 110, the processor 120, the memory 130, etc.) of the electronic device 101 to at least one of the application programs 147. For example, the middleware 143 may perform scheduling or load balancing with respect to the one or more task requests by processing the one or more task requests based on the priority given to the at least one of the application programs 147.

The API 145 is an interface used for the application 147 to control a function provided by the kernel 141 or the middleware 143, and may include, for example, at least one interface or function (e.g., a command) for file control, window control, image processing or character control.

The I/O interface 150 serves as an interface for delivering, for example, a command or data input from a user or another external device to other component(s) of the electronic device 101. The I/O interface 150 may also output a command or data received from other component(s) of the electronic device 101 to a user or another external device.

The display 160 may include, for example, a liquid crystal display (LCD), a light emitting diode (LED) display, an organic light emitting diode (OLED) display, a microelectromechanical system (MEMS) display, or an electronic paper display. The display 160 may, for example, display various contents (e.g., a text, an image, video, an icon, a symbol, etc.) to users. The display 160 may include a touch screen, and receives a touch, a gesture, proximity, or a hovering input, for example, by using an electronic pen or a part of a body of a user.

The communication interface 170 establishes communication between the electronic device 101 and an external device (e.g., a first external electronic device 102, a second external electronic device 104, or a server 106). For example, the communication interface 170 may be connected to a network 162 through wireless communication or wired communication to communicate with an external device (e.g., the second external electronic device 104 or the server 106).

Wired communication may use, for example, as a cellular communication protocol, at least one of, for example, long-term evolution (LTE), LTE advance (LTE-A), code division multiple access (CDMA), wideband CDMA (WCDMA), universal mobile telecommunications system (UMTS), wireless broadband (WiBro), global system for mobile communications (GSM), and so forth. The wired communication may include, for example, short-range communication 164. The short-range communication 164 may include, for example, at least one of wireless fidelity (WiFi), Bluetooth, near field communication (NFC), a global navigation satellite system (GNSS), and the like. Depending on a usage area or bandwidth, the GNSS may include, for example, at least one of a global positioning system (GPS), a global navigation satellite system (Glonass), a Beidou navigation satellite system ("Beidou"), and Galileo, the European global satellite-based navigation system. Hereinbelow, "GPS" may be used interchangeably with "GNSS". The wired communication may include, for example, at least one of a USB (universal serial bus), a high definition multimedia interface (HDMI), a recommended standard (RS)-232, a plain old telephone service (POTS), and so forth. The network 162 may include a telecommunications network, for example, at least one of a computer network (e.g., a local area network (LAN) or a wide area network (WAN)), Internet, and a telephone network.

Each of the first electronic device 102 and the second electronic device 104 may be a device of the same type as or a different type than the electronic device 101. According to an embodiment of the present disclosure, the server 106 may include a group of one or more servers. According to various embodiments of the present disclosure, some or all of operations performed by the electronic device 101 may be performed in another electronic device or a plurality of electronic devices (e.g., the electronic device 102 or 104, or the server 106). According to an embodiment of the present disclosure, when the electronic device 101 has to perform a function or a service automatically or at a request, the electronic device 101 may request another device (e.g., the electronic device 102 or 104 or the server 106) to perform at least some functions associated with the function or the service instead of or in addition to executing the function or the service. The another electronic device (e.g., the electronic device 102 or 104 or the server 106) may execute the requested function or additional function and deliver the execution result to the electronic device 101. The electronic device 101 may then process or further process the received result to provide the requested function or service. To this end, for example, cloud computing, distributed computing, or client-server computing may be used.

Figure 2:
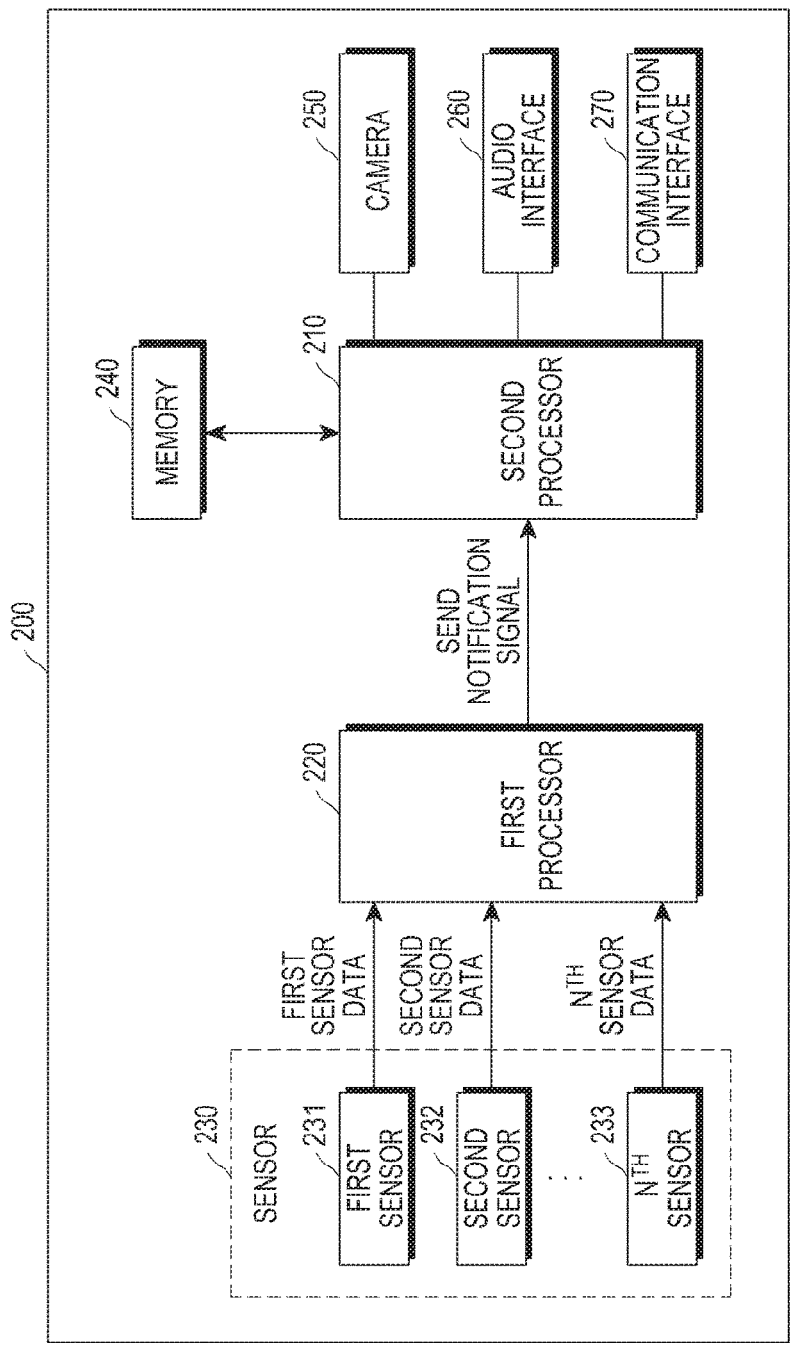
FIG. 2 illustrates a block diagram of an electronic device according to various embodiments of the present disclosure.

FIG. 2 illustrates a block diagram of an electronic device according to various embodiments of the present disclosure.

Referring to FIG. 2, an electronic device 200 may include at least one processor (e.g., a first processor 220 or a second processor 210), a sensor 230, and a memory 240.

According to various embodiments of the present disclosure, the first processor 220 (e.g., a sensor hub, a low energy processor, etc.) may operate with lower power than the second processor 210. The first processor 220 transmits data received from the sensor 230 to the second processor 210. For example, the first processor 220 may combine the received data to generate quaternion data or to calculate the combined data as particular data (e.g., the number of steps, a heart rate, a blood sugar level, a moving direction, etc.) and transmits corresponding data to the second processor 210.

According to various embodiments of the present disclosure, the first processor 220 functions as a sensor hub by determining that data is sensed through a sensor included in the sensor 230 and processing the sensed data into data that is processible by the electronic device 200.

The second processor 210 controls the overall operation of the electronic device 200. For example, the second processor 210 may identify data received from the first processor 220, include time information in each data, and store the data.

According to various embodiments of the present disclosure, the first processor 220 may send a notification signal to the second processor 210 based on reception of data from the sensor 230. The second processor 210 identifies time information upon identifying the notification signal (e.g., an interrupt signal) with respect to data. For example, the second processor 210 may be electrically connected with a time source (not shown) that generates time information or may be configured to generate time information.

According to various embodiments of the present disclosure, the second processor 210 may determine reception of a signal input through a preset channel or connection (e.g., inter integrated circuit (I2C), serial peripheral interface (SPI), universal asynchronous receiver/transmitter (UART), etc.) or a signal including a preset voltage variation value as reception of the notification signal.

According to various embodiments of the present disclosure, the second processor 210 determines first identification information (e.g., an index) regarding data, upon receiving the notification signal. For example, the second processor 210 may increase an index based on the number of times the notification signal is received.

According to various embodiments of the present disclosure, the second processor 210 associates sensor data received from the first processor 220 with time information obtained based on the notification signal and stores the associated data in the memory 240.

The sensor 230 may include at least one sensor (e.g., a first sensor 231, a second sensor 232, or an nth sensor 233). For example, the at least one sensor may include at least one of an acceleration sensor, a gyroscope sensor, a geomagnetic sensor, a barometer sensor, a light sensor, a proximity sensor, a temperature sensor, a humidity sensor, a gesture sensor, a grip sensor, a color sensor (e.g., an RGB sensor), a biometric sensor (e.g., a fingerprint sensor, an iris sensor, a heart rate sensor, or a blood sugar sensor), an ultraviolet (UV) sensor, a position sensor, an environment sensor, a voice sensor, and so forth, and the sensor 230 transmits data measured from each sensor as low-energy data to the first processor 220.

For example, the acceleration sensor may measure data corresponding to the strength of a force or an acceleration impulse per axis, which works on x, y, and z axes with respect to a reference position of the electronic device 200.

The gyroscope sensor may measure data corresponding to a measurement value (Rad/s) of a rotational velocity (angular velocity) working on x, y, and z axes with respect to a reference position of the electronic device 200.

The geomagnetic sensor may measure data corresponding to a measurement value (uT) or an azimuthal angle of a geomagnetic field measured in the electronic device 200.

The barometer sensor may measure data corresponding to a pressure value (hPa) measured in the electronic device 200 or an altitude (m) based on the pressure value.

The light sensor may measure data corresponding to an intensity of radiation (Lux) or an intensity of light measured around the electronic device 200.

The proximity sensor may measure proximity of an object to a particular surface of the electronic device 200 and measure a distance between the approaching object and the electronic device 200 according to the strength of the measured data.

The temperature sensor may measure data corresponding to a temperature measured around the electronic device 200.

The humidity sensor may measure data corresponding to a humidity (%) measured around the electronic device 200.

The biometric sensor may measure may measure biometric information (e.g., a fingerprint, an iris, a retina, a heartbeat, etc.) and measure data corresponding to image or feature point information corresponding to the measured biometric information (e.g., a fingerprint, an iris, a retina, a heartbeat, etc.) of the user, data corresponding to velocity or concentration information of biometric information (e.g., a blood sugar level), etc.

The UV sensor may measure data corresponding to ultraviolet rays.

The image sensor may sense image data input through the camera 250 positioned on a front surface or a rear surface of the electronic device 200.

The position sensor may identify a signal received from a satellite or a signal (e.g., beacon) received through short-range communication (WiFi, BT) and measure data corresponding to latitude/longitude information or distance, direction, etc., based on the strength or time information of the received signal.

The environment sensor may measure data corresponding to the amount concentration, density, or the like of a particular gas measured around the electronic device 200.

The voice sensor may identify a voice signal measured through the audio interface 260 and measure data corresponding to a wavelength or intensity of the identified voice signal.

The memory 240 stores at least one data and time information regarding respective data. For example, the time information may include a time information value identified upon generation of a notification signal (e.g., an interrupt signal) and an index value of particular data increased based on the notification signal in the second processor 210.

The camera 250 captures an image. For example, the captured image may include a frame divided horizontally or vertically.

According to various embodiments of the present disclosure, each frame may be captured in a shaken state due to movement of the electronic device 200, and the electronic device 200 senses the shaken state based on data measured by the sensor 230 and the second processor 210 corrects shake of each frame based on the data measured by the sensor 230.

The audio interface 260 processes internal data into voice data and outputs the voice data, and converts the voice data input from an external source into data processible by the electronic device 200. The audio interface 260 identifies input/output time of each voice data as time information of particular data.

The communication interface 270 transmits and receives data to and from an external electronic device. For example, the communication interface 270 may include at least one of a cellular interface, a WiFi interface, a BT interface, a GNSS interface (e.g., a GPS interface), an NFC interface, and an RF interface, and may include other various interfaces for controlling data communication with an external device.

An electronic device according to various embodiments of the present disclosure may include a sensor (e.g., the sensor 230), a first processor (e.g., the first processor 220) capable of obtaining data sensed using the sensor, and a second processor (e.g., the second processor 210) capable of executing an application, and the second processor is configured to receive a notification signal corresponding to the data from the first processor, to determine time information and first identification information that correspond to the notification signal in response to the reception, to receive the data and second identification information corresponding to the notification signal from the first processor, to associate the data with the time information at least based on the first identification information and the second identification information, and to provide the data associated with the time information to the application.

The electronic device according to various embodiments of the present disclosure may further include a memory (e.g., the memory 240), and the second processor is configured to determine the first identification information based on identification information corresponding to the second identification information, and to associate the data with the time information at least based on the identification and store the data and the time information in the memory.

The second processor according to various embodiments of the present disclosure is configured to generate first index information corresponding to the notification signal and to generate second index information at least based on the first index information in response to reception of another notification signal.

The electronic device according to various embodiments of the present disclosure may further include another sensor capable of sensing first data associated with the electronic device, and the second processor is configured to receive another data from the another sensor and to determine third index information and another time information which correspond to the another data from the time information.

The electronic device according to various embodiments of the present disclosure may further include a camera (e.g., the camera 250), and the second processor is configured to receive image data from the camera and to identify time information of the image data or time information of each frame of the image data.

The second processor according to various embodiments of the present disclosure is configured to identify a first frame including time information corresponding to the third index information among at least one frames included in the image data and to correct a position in the image data in which the first frame is included at least based on information included in the another data.

The second processor according to various embodiments of the present disclosure is configured to identify the time information through the application and to identify data corresponding to the application among plural data sensed by the sensor at least based on the identified time information.

According to various embodiments of the present disclosure, the notification signal includes an interrupt signal, and the second processor is configured to stop an operation other than a preset operation upon receiving the interrupt signal and to obtain the time information.

The electronic device according to various embodiments of the present disclosure may include a sensor, a first processor capable of obtaining data sensed using the sensor, and a second processor capable of executing an application, and the first processor is configured to send a notification signal corresponding to the data to the second processor, to determine identification information corresponding to the data, and to transmit the data and identification information corresponding to the data to the second processor.

The first processor according to various embodiments of the present disclosure is configured to receive another data through the sensor, to identify time information corresponding to the notification signal, and to transmit another data and the time information to the second processor.

Figure 3:
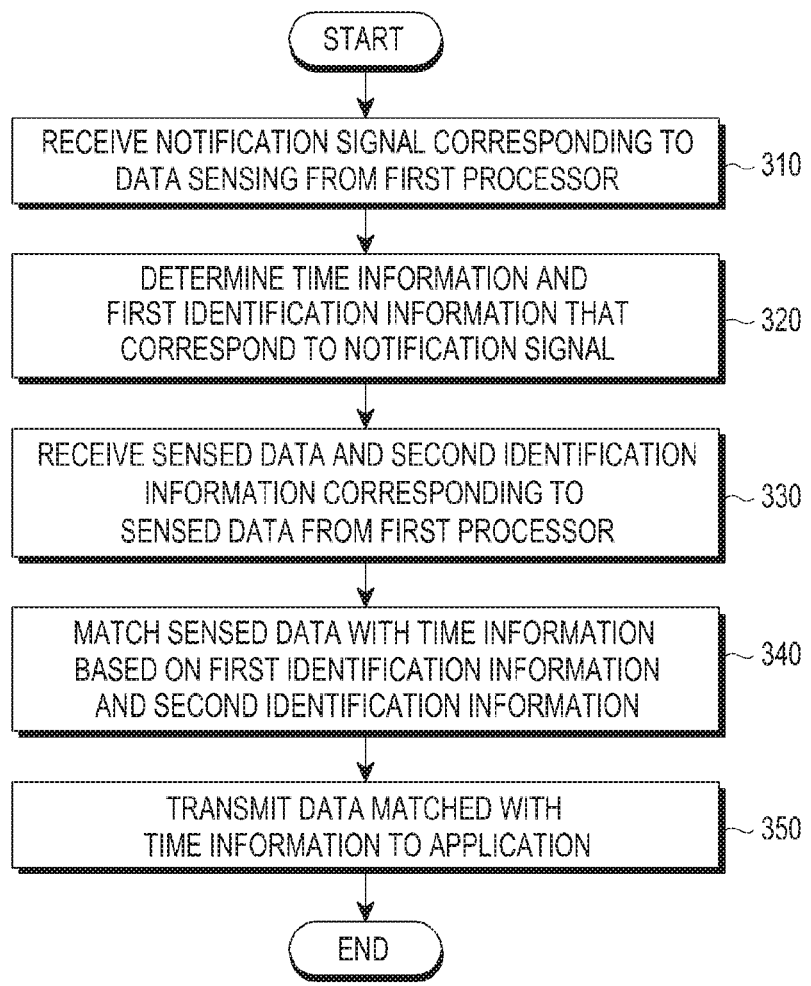
FIG. 3 illustrates a flowchart of an operation of associating sensor data with time information in a second processor according to various embodiments of the present disclosure.

FIG. 3 illustrates a flowchart of an operation of associating sensor data with time information in a second processor according to various embodiments of the present disclosure.

Referring to FIG. 3, in operation 310, the second processor (e.g., the second processor 210) receives a notification signal corresponding to data sensing from the first processor (e.g., the first processor 220). For example, the notification signal, as an interrupt signal, may include data requesting generation of time information.

In operation 320, the second processor 210 determines time information and first identification information which correspond to the notification signal. For example, the time information may be generated as the notification signal is received, and the first identification information may correspond to an index increase value or index increment counted based on reception of the notification signal.

According to various embodiments of the present disclosure, the first identification information is identification information for identifying the notification signal, and may include an index value given according to an order of a notification signal received from the first processor 220. For example, if a first notification signal is received from the first processor 220, the second processor 210 may determine an index value as '1', and determine an index value for a second notification signal received from the second processor 210 as '2'.

In operation 330, the second processor (e.g., the second processor 210) receives data sensed from the first processor 220 and second identification information corresponding to the notification signal (e.g., the interrupt signal). For example, the second notification signal may correspond to an index increment counted as the notification signal is transmitted.

According to various embodiments of the present disclosure, an electronic device may include an index value for identifying data received from the sensor for the second identification information. For example, when the first processor (e.g., the low-energy processor) delivers the first notification signal to the second processor (e.g., the AP), the first processor 220 may set an index value for the first notification signal to '1'. When the first processor (e.g., the low-energy processor) delivers the second notification signal to the second processor (e.g., the AP), the first processor 220 may set an index value for the second notification signal to '2'.

In operation 340, the second processor (e.g., the second processor 210) matches the sensed data with time information based on the first identification information and the second identification information. For example, the second processor may compare first identification information associated with the time information with second identification information associated with the data received from the first processor, and match the data with the time information if the two identification information is identical to each other.

According to various embodiments of the present disclosure, the second processor identifies the first identification information corresponding to the second identification information. For example, if the second identification information is '1', the second processor may determine identification information in which the first identification is '1', and match time information corresponding to the first identification information with the sensed data.

In operation 350, the second processor (e.g., the second processor 210) transmits the data matched with the time information to an application. For example, the electronic device may identify time information regarding data received from another module or sensor through the data matched with the time information.

Figure 4:
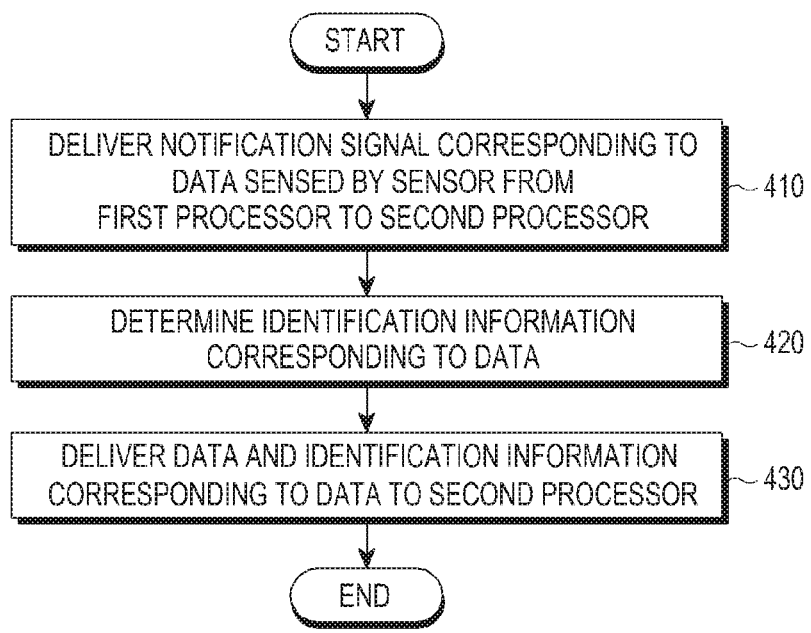
FIG. 4 illustrates a flowchart of an operation of associating sensor data with time information by transmitting an alarm signal to a second processor, in a first processor, according to various embodiments of the present disclosure.

FIG. 4 illustrates a flowchart an operation of associating sensor data with time information by transmitting an alarm signal to a second processor, in a first processor, according to various embodiments of the present disclosure.

Referring to FIG. 4, in operation 410, the first processor (e.g., the first processor 220) delivers a notification signal corresponding to data sensed by the sensor to the second processor.

In operation 420, the first processor determines identification information corresponding to the sensed data. For example, the identification information may include an index value increased corresponding to the notification signal, and the index value may increase corresponding to the number of times the notification signal is sent.

In operation 430, the first processor transmits the data and identification information corresponding to the data to the second processor (e.g., the second processor 210).

Figure 5:
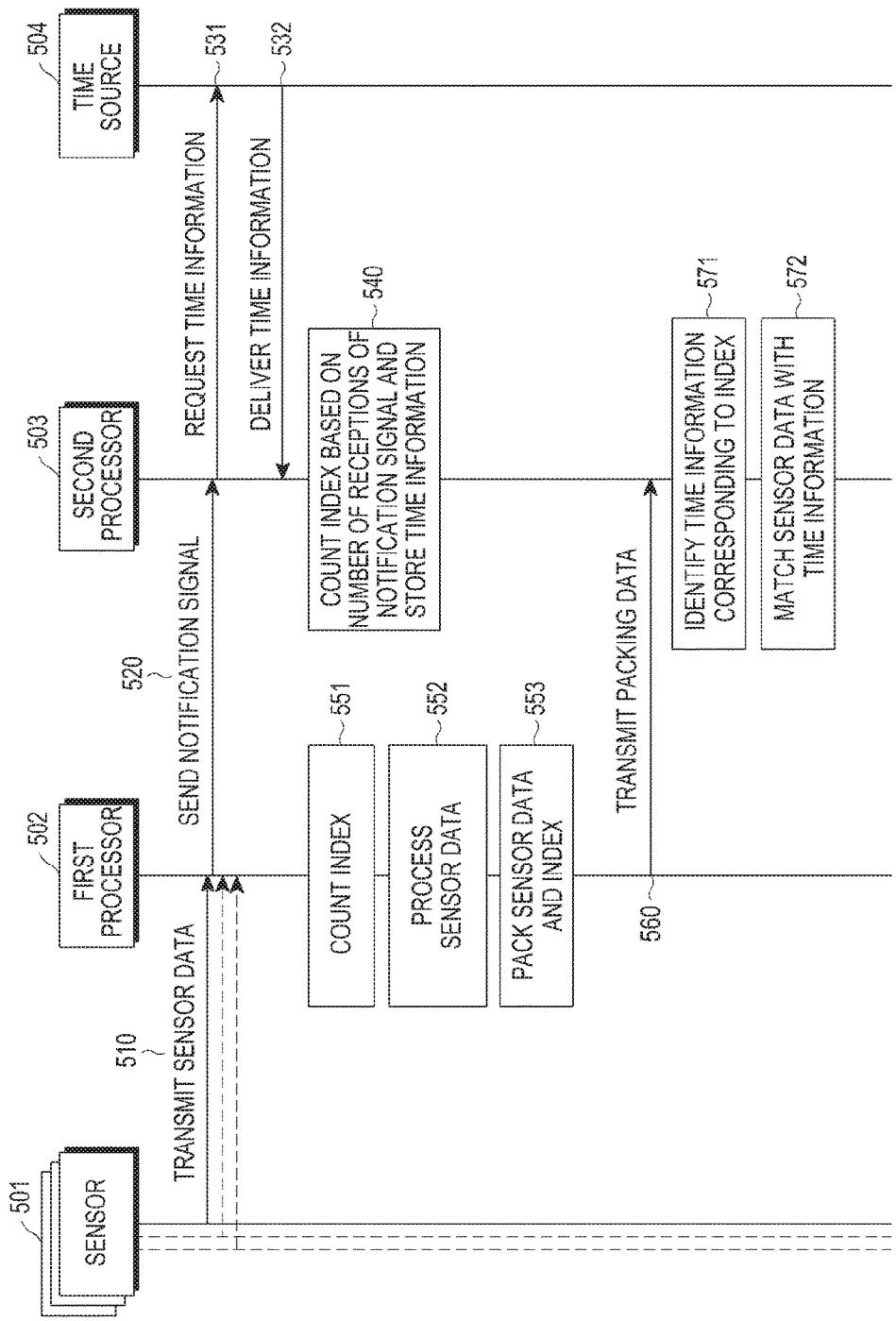
FIG. 5 illustrates a flowchart operations between a sensor, processors, and a time source to associate sensor data of data with time information in an electronic device according to various embodiments of the present disclosure.

FIG. 5 illustrates a flowchart of operations between a sensor, processors, and a time source to associate sensor data of data with time information in an electronic device according to various embodiments of the present disclosure.

Referring to FIG. 5, in operation 510, a sensor 501 transmits sensed sensor data to a first processor (e.g., a low-energy processor) 502. For example, upon identifying the sensor data sensed by at least one sensor, the sensor 501 may transmit the sensor data to the first processor 502 driven with low energy among processors of the electronic device.

In operation 520, the first processor 502 sends a notification signal (e.g., the interrupt signal) to a second processor (e.g., a main processor or an application processor) 503. For example, the notification signal may include data that requests the second processor 503 to stop an ongoing operation and to obtain time information for the sensor data.

In operation 531, the second processor 503 sends a request for time information to a time source 504.

In operation 532, the time source 504 generates time information and delivers the generated time information to the second processor 503 in response to the time information request. For example, the time information is used to determine a point in time in which the sensor data is sensed, and may correspond to a point in time in which the notification signal is transmitted from the first processor 502 to the second processor 503.

According to various embodiments of the present disclosure, the second processor 503 and the time source 504 are illustrated as separate elements, but if at least one of functions of the time source 504 is performed in the second processor 503, the time source 504 may be omitted or changed.

In operation 540, the second processor 503 counts an index based on the number of times the notification signal is received, and stores the index and the time information.

According to various embodiments of the present disclosure, the second processor 503 determines an index value to identify each notification signal. For example, if the second processor 503 may determine an index value of the first notification signal as '1', the second processor 503 may determine an index value for another notification signal as '2' which is increased by 1 from the index value for the first notification signal.

In operation 551, the first processor 502 counts an index. For example, the first processor 502 may increase an index value corresponding to a point in time in which the notification signal is sent.

In operation 552, the first processor 502 processes received sensor data. For example, the processing operation may include delivering the received sensor data to an internal algorithm of the first processor 502 or converting the received sensor data into data processible by the second processor 503.

In operation 553, the first processor 502 packs a corresponding index value in the processed sensor data. For example, the packing operation may include determining an index value increased for each sensor data, including the index value in corresponding sensor data, and storing the sensor data.

In operation 560, the first processor 502 transmits the packing data to the second processor 503.

In operation 571, the second processor 503 identifies time information corresponding to the packing data based on the index value. For example, the second processor 503 may identify time information including the same index as the index included in the packing data.

In operation 572, the second processor 503 matches the sensor data included in the packing data with the time information. For example, the second processor 503 may identify time information corresponding to the index included in the packing data, include a corresponding time information value in the received sensor data, and store the sensor data.

According to various embodiments of the present disclosure, the first processor 502 counts an index with respect to sending of a notification signal, and the second processor 503 identifies index increase and time information with respect to reception of a notification signal. For example, the notification signal is sent as sensor data is sensed, and a time information value for the sensed sensor data may be synchronized in the first processor 502 and the second processor 503.

Figure 6:
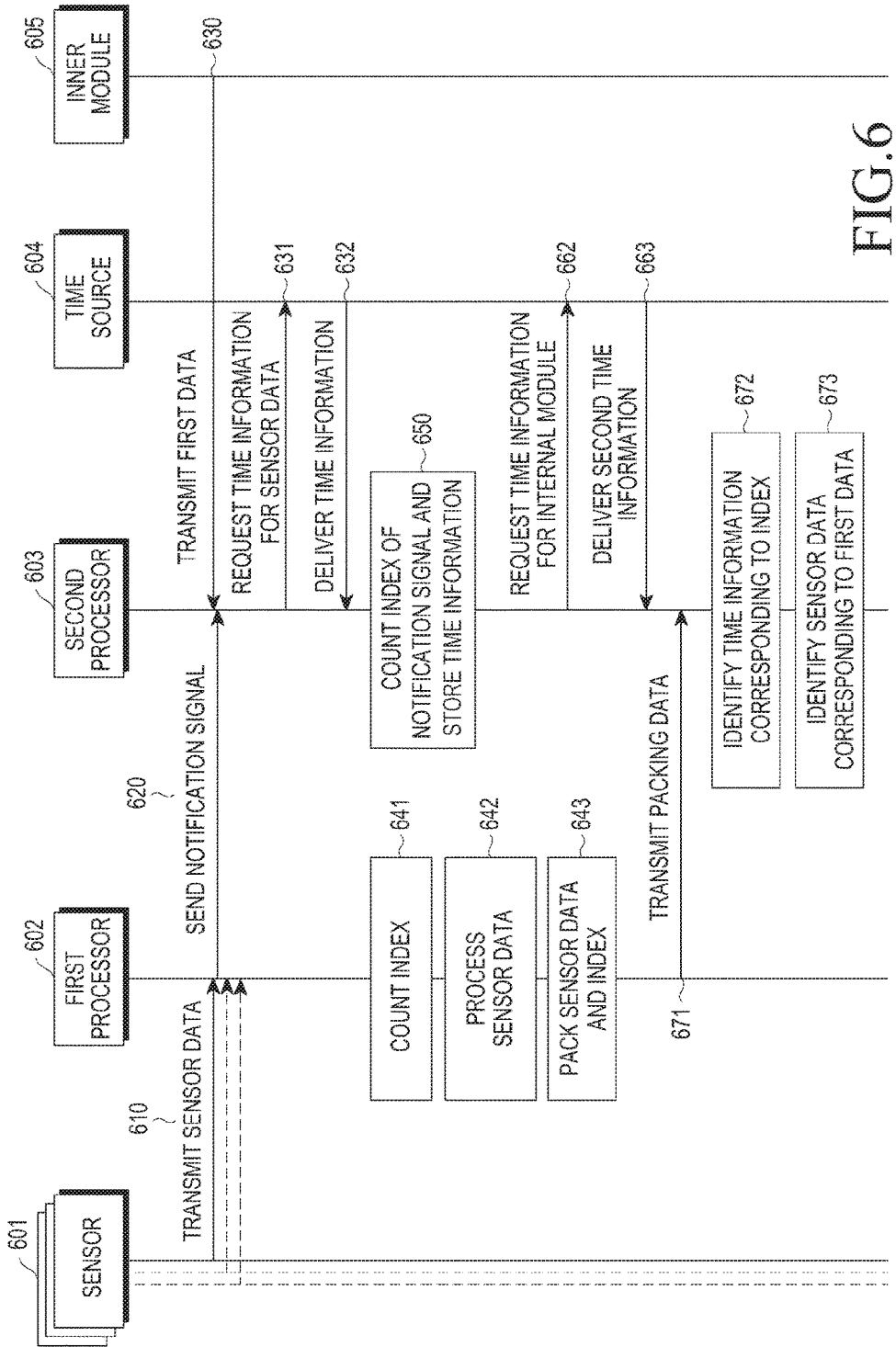
FIG. 6 illustrates a flowchart of operations between a sensor, processors, a time source, and an internal module to associate sensor data with time information in an electronic device according to various embodiments of the present disclosure.

FIG. 6 illustrates a flowchart of operations between a sensor, processors, a time source, and an internal module to associate sensor data with time information in an electronic device according to various embodiments of the present disclosure.

Referring to FIG. 6, in operation 610, a sensor 601 transmits sensed sensor data to a first processor (e.g., a low-energy processor) 602. For example, upon identifying the sensor data sensed by at least one sensor, the sensor 601 may transmit the sensor data to the first processor 602 driven with low energy among processors of the electronic device.

In operation 620, the first processor 602 sends a notification signal to the second processor 603. For example, the notification signal may include data that requests the second processor 603 to stop an ongoing operation and to obtain time information for the transmitted sensor data.

In operation 630, the first processor 605 transmits first data to the second processor 603. For example, the internal module 605 may include at least one element (e.g., a camera, a communication interface, or an I/O interface) included in the electronic device or electrically connected with the electronic device.

According to various embodiments of the present disclosure, data generated or identified using the at least one module is delivered and processed in the second processor 603. For example, the second processor 603 may determine an index of sensor data to identify sensor data corresponding to data transmitted through the at least one module.

In operation 631, the second processor 603 sends a request for first time information for the sensor data to a time source 604.

In operation 632, the time source 604 generates the first time information and delivers the generated first time information to the second processor 603 in response to the time information request. For example, the first time information is used to determine a point in time in which the sensor data is sensed, and may correspond to a point in time in which the notification signal is transmitted from the first processor 602 to the second processor 603.

According to various embodiments of the present disclosure, the second processor 603 and the time source 604 are illustrated as separate elements, but if at least one of functions of the time source 604 is performed in the second processor 603, the time source 604 may be omitted or changed.

In operation 641, the first processor 602 counts an index. For example, the first processor 602 may increase an index value according to the number of times the notification signal is sent or increase an index value corresponding to a time elapsed from sending of the notification signal to a particular point in time.

In operation 642, the first processor 602 processes received sensor data.

In operation 643, the first processor 602 packs a corresponding index value in the received sensor data.

In operation 650, the second processor 603 counts the notification signal and stores first time information corresponding to a count value of the notification signal. For example, the second processor 603 may count an index value for a notification signal corresponding to the number of times the notification signal is received or a time elapsed from reception of the notification signal.

In operation 662, the second processor 603 sends a request for time information for the internal module 605 to the time source 604. For example, the time information for the internal module 605 may be requested as the first data is received from the internal module 605, and may correspond to a point in time when the first data is identified by the second processor 603.

In operation 663, the time source 604 generates second time information and delivers the generated second time information to the second processor 603 in response to the time information request for the internal module 605.

In operation 671, the first processor 602 transmits the packing data to the second processor 603.

In operation 672, the second processor 603 identifies time information corresponding to the index included in the packing data.

In operation 673, the second processor 603 identifies the sensor data corresponding to the first data. For example, the second processor 603 may identify first time information indicating a point in time corresponding to a point in time indicated by second time information that is time information of the first data, and identify the sensor data packed together with the first time information.

According to various embodiments of the present disclosure, the second processor 603 identifies time information of data transmitted from at least one module and identifies sensor data including time information corresponding to the identified time information. The sensor data and the data transmitted from the at least one module may be temporally synchronized with each other.

Figure 7:
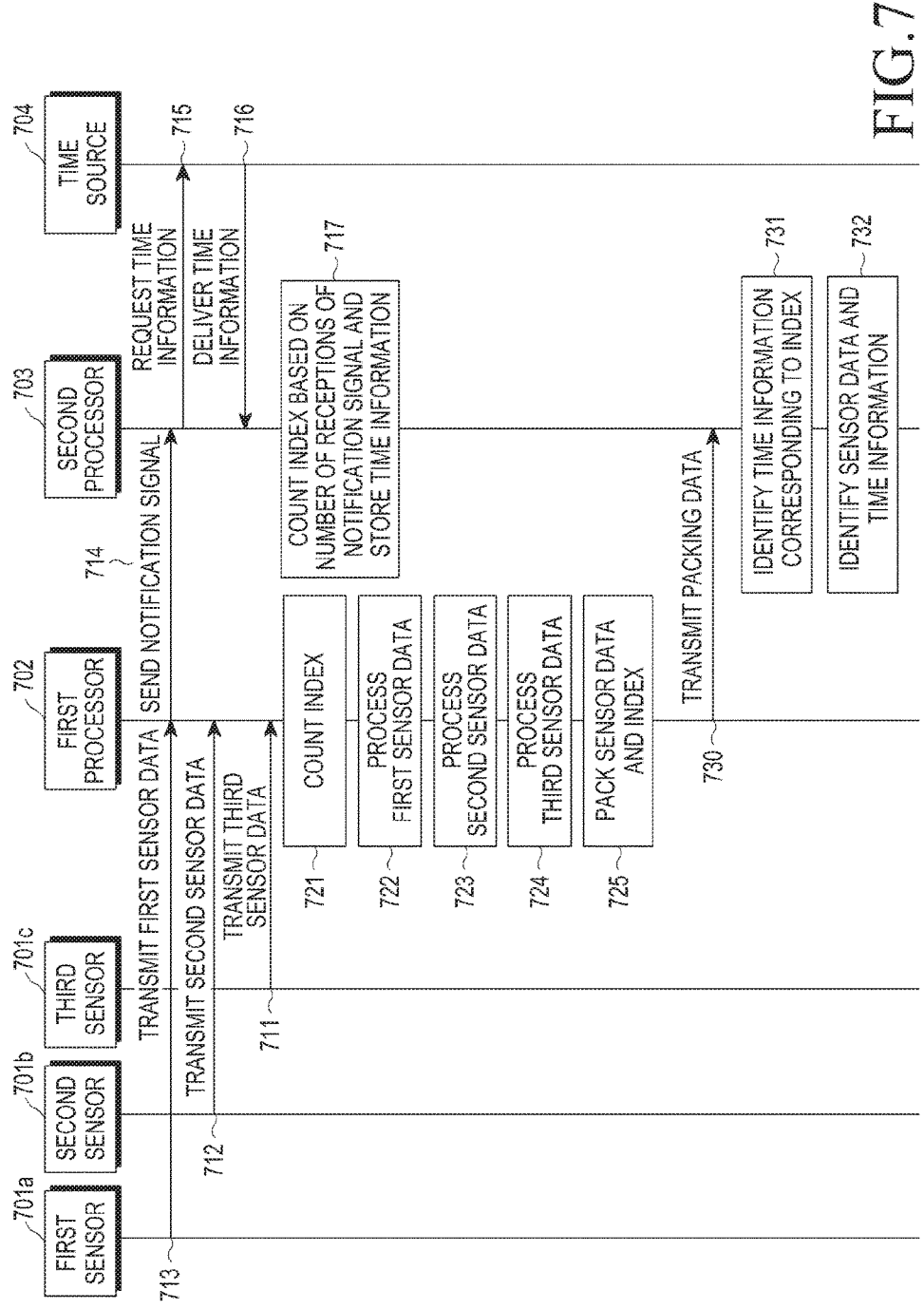
FIG. 7 illustrates a flowchart of operations between at least one sensor, processors, and a time source to associate sensor data generated within a predetermined time period with time information in an electronic device according to various embodiments of the present disclosure.

FIG. 7 illustrates a flowchart of operations between at least one sensor, processors, and a time source to associate sensor data generated within a predetermined time period with time information in an electronic device according to various embodiments of the present disclosure.

Referring to FIG. 7, a third sensor 701c transmits sensed third sensor data to a first processor 702 in operation 711, a second sensor 701b transmits sensed second sensor data to the first processor 702 in operation 712, and a first sensor 701a transmits sensed first sensor data to the first processor 702 in operation 713.

According to various embodiments of the present disclosure, the first sensor data, the second sensor data, and the third sensor data are transmitted to the first processor 702 at a particular point in time (e.g., a first point in time). For example, the particular point in time may include a time period within a preset time range.

According to various embodiments of the present disclosure, the first processor 702 senses data generated from a particular sensor at predetermined intervals. For example, the first processor 702 and the second processor 703 may identify information included in particular sensor data to identify information about a sensor that has transmitted the sensor data or determine identification information of the sensor data.

In operation 714, the first processor 702 sends a notification signal to the second processor 703. For example, the notification signal may be sent to the second processor 703 at a first point in time in which the sensor data is received.

In operation 715, the second processor 703 sends a request for time information corresponding to the first point in time to a time source 704.

In operation 716, the time source 704 generates the time information corresponding to the first point in time and delivers the generated time information to the second processor 703 in response to the time information request.

According to various embodiments of the present disclosure, the second processor 703 and the time source 704 are illustrated as separate elements, but if at least one of functions of the time source 704 is performed in the second processor 703, the time source 704 may be omitted or changed.

In operation 717, the second processor 703 counts an index based on the number of times the notification signal is received, and stores the index together with the time information. For example, the second processor 703 may determine the number of times the notification signal is sent or an index increment from the first point in time, count the notification signal, and store time information requested for the notification signal together with the counted notification signal.

According to various embodiments, as notification signals for the first data, the second data, and the third data are sent in the first point in time, time information for the sensor data may be assigned identically.

In operation 721, the first processor 702 counts an index. For example, the first processor 702 may increase an index value from a point in time in which the notification signal is sent up to a point in time in which another sensor data is received.

In operation 722, the first processor 702 processes received first sensor data.

In operation 723, the first processor 702 processes received second sensor data.

In operation 724, the first processor 702 processes received third sensor data.

In operation 725, the first processor 702 packs received sensor data and an index corresponding to respective sensor data. For example, the received sensor data may be packed to include the same index increment as being identified by the first processor 702 in the first point in time.

In operation 730, the first processor 702 transmits the packing data to the second processor 703.

In operation 731, the second processor 703 identifies an index of particular sensor data included in the packing data and identifies time information corresponding to the index.

In operation 732, the second processor 703 matches each sensor data included in the received packing data with time information corresponding to the index of the sensor data.

Figure 8A:
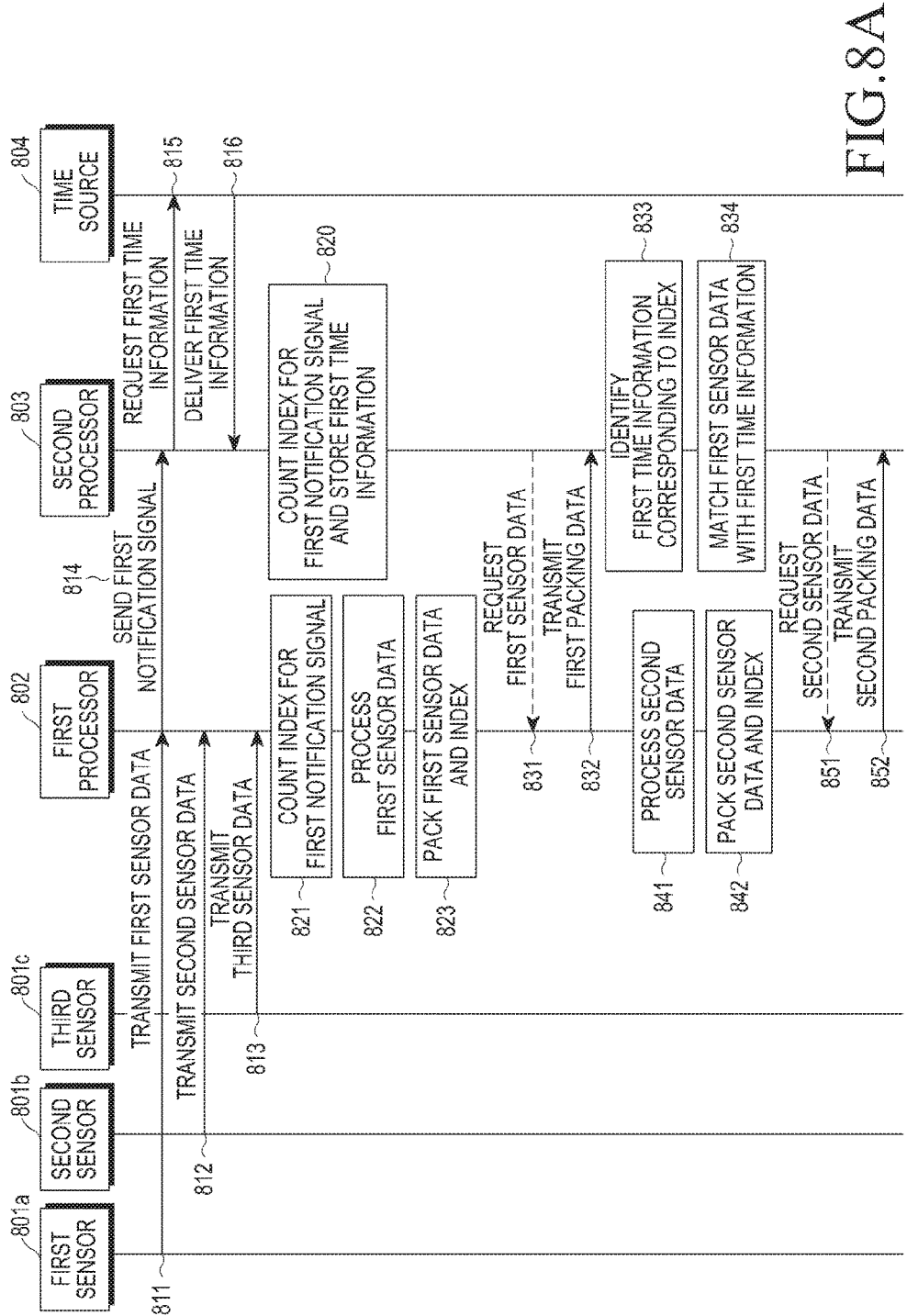
FIG. 8A illustrates a flowchart of operations between at least one sensor, processors, and a time source to associate sensor data generated by a plurality of sensors with time information in an electronic device according to various embodiments of the present disclosure.

FIG. 8A illustrates a flowchart of operations between at least one sensor, processors, and a time source to associate sensor data generated by a plurality of sensors with time information in an electronic device according to various embodiments of the present disclosure.

Referring to FIG. 8A, a first sensor 801a transmits sensed first sensor data to a first processor 802 in operation 811, a second sensor 801b transmits sensed second sensor data to the first processor 802 in operation 812, and a third sensor 801c transmits sensed third sensor data to the first processor 802 in operation 813.

According to various embodiments of the present disclosure, the first sensor data, the second sensor data, and the third sensor data are transmitted to the first processor 802 at a particular point in time (e.g., a first point in time). For example, an order of transmission of the first through third sensor data to the second processor 803 in the first point in time may be determined depending on the degree of importance or a type of the sensor data.

In operation 814, the first processor 802 sends a notification signal to the second processor 803. For example, the notification signal may be sent to the second processor 803 at a first point in time in which the sensor data is received.

In operation 815, the second processor 803 sends a request for time information corresponding to the first point in time to a time source 804.

In operation 816, the time source 804 generates first time information corresponding to the first point in time and delivers the generated first time information to the second processor 803 in response to the time information request.

According to various embodiments of the present disclosure, the second processor 803 and the time source 804 are illustrated as separate elements, but if at least one of functions of the time source 804 is performed in the second processor 803, the time source 804 may be omitted or changed.

In operation 820, the second processor 803 counts an index based on the number of times the first notification signal is received as the notification signal, and stores the counted index value as the first time information. For example, the second processor 803 may identify the number of times the first notification signal is sent or the number of times a sensing period for sensor data is repeated from the first point in time, and count an index as many times as the identified number of times.

According to various embodiments, as notification signals for the first data, the second data, and the third data are sent in the first point in time, time information for the sensor data may be assigned identically.

In operation 821, the second processor 802 counts an index based on the number of times the first notification signal is sent as the notification signal. For example, the first processor 802 may increase an index value as many times as the notification signal is sent.

According to various embodiments of the present disclosure, the first processor 802 may identify, for at least one sensor data that performs sensing at predetermined intervals, the number of times the predetermined interval is repeated from the first point in time up to counting of the index, and determine the identified number of times as an index increment. The index increment at the first point in time may be determined as time information for the at least one sensor data.

In operation 822, the first processor 802 processes received first sensor data.

In operation 823, the first processor 802 packs the first sensor data together with an index increment corresponding to the first sensor data and processes them as first packing data.

In operation 831, the second processor 803 requests the first sensor data. For example, the request may request sensor data of a particular type or sensor data sensed at a particular point in time.

According to various embodiments of the present disclosure, the first processor 802 is configured to transmit sensor data received for a predetermined time to the second processor 803, and in this case, the above-described operation 831 may be omitted.

In operation 832, the first processor 802 transmits the first packing data to the second processor 803. The first processor 802 transmits the first packing data in response to a request for the first sensor data from the second processor 803 or at predetermined intervals or points in time.

In operation 833, the second processor 803 identifies an index included in the first packing data and identifies first time information corresponding to the index. For example, the first time information may correspond to an index value increased according to the number of times the first notification signal is sent.

In operation 834, the second processor 803 matches the received first sensor data with the first time information.

In operation 841, the first processor 802 processes received second sensor data.

In operation 842, the first processor 802 packs the second sensor data together with a second index increment corresponding to the second sensor data and processes them as second packing data. For example, the second index increment may correspond to an index value increased according to the number of times the first notification signal is sent.

In operation 851, the second processor 803 requests the second sensor data. For example, the request may request sensor data of a particular type or sensor data sensed at a particular point in time.

According to various embodiments of the present disclosure, the first processor 802 is configured to transmit sensor data received for a predetermined time to the second processor 803, and in this case, the above-described operation 851 may be omitted.

In operation 852, the first processor 802 transmits the second packing data to the second processor 803. The first processor 802 transmits the second packing data in response to a request for the second sensor data from the second processor 803 or at predetermined intervals or points in time.

Figure 8B:
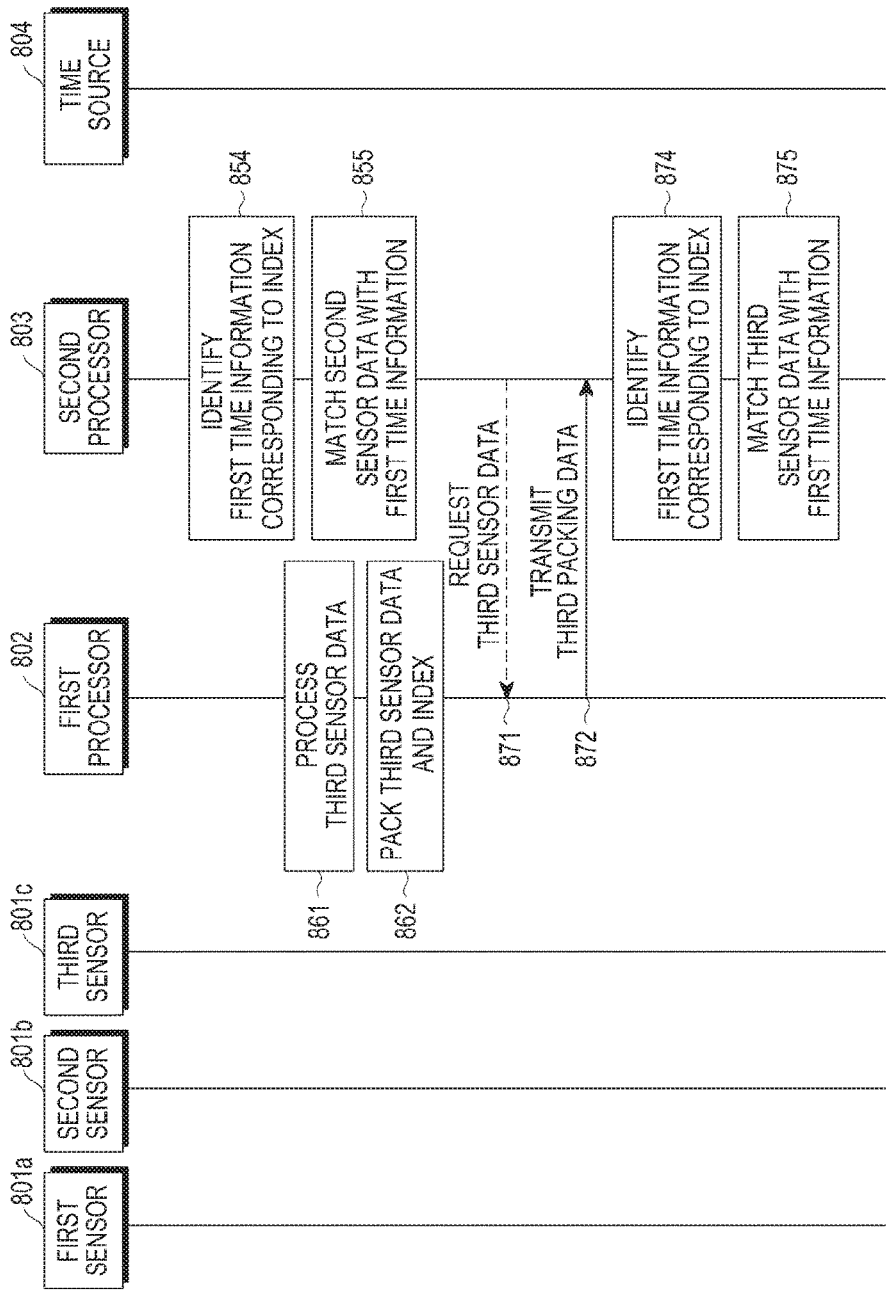
FIG. 8B illustrates a flowchart of operations between at least one sensor, processors, and a time source to associate sensor data with time information in an electronic device according to various embodiments of the present disclosure.

Referring to FIG. 8B, in operation 853, the second processor 803 identifies the second index increment included in the second packing data and identifies second time information corresponding to the second index increment. For example, the second time information may correspond to an index value increased according to the number of times the first notification signal is sent.

In operation 854, the second processor 803 matches the received second sensor data with the second time information.

In operation 861, the first processor 802 processes received third sensor data.

In operation 862, the first processor 802 packs the third sensor data together with a third index increment corresponding to the third sensor data and processes them as third packing data. For example, the third index increment may correspond to an index value increased according to the number of times the first notification signal is sent.

In operation 871, the second processor 803 requests the third sensor data. For example, the request may request sensor data of a particular type or sensor data sensed at a particular point in time.

According to various embodiments of the present disclosure, the first processor 802 is configured to transmit sensor data received for a predetermined time to the second processor 803, and in this case, the above-described operation 871 may be omitted.

In operation 872, the first processor 802 transmits the third packing data to the second processor 803. The first processor 802 transmits the third packing data in response to a request for the third sensor data from the second processor 803 or at predetermined intervals or points in time.

In operation 874, the second processor 803 identifies a third index increment included in the third packing data and identifies third time information corresponding to the third index increment. For example, the third time information may correspond to an index value increased according to the number of times the first notification signal is sent.

In operation 875, the second processor 803 matches the received third sensor data with the third time information.

According to various embodiments of the present disclosure, a method for associating data with time information in an electronic device includes receiving a notification signal corresponding to data sensed using the sensor from a first processor, determining time information and first identification information that correspond to the notification signal by using a second processor in response to the reception, receiving the data and second identification information corresponding to the notification signal from the first processor, associating the data with the time information at least based on the first identification information and the second identification information, and providing the data associated with the time information to an application by using the second processor.

A method for associating data with time information in an electronic device according to various embodiments of the present disclosure may further include determining the first identification information as identification information corresponding to the second identification information, and associating the data with the time information at least based on the determination and storing the data and the time information.

The method for associating data with time information in the electronic device according to various embodiments of the present disclosure may further include generating first index information corresponding to the notification signal and generating second index information at least based on the first index information in response to reception of another notification signal.

The method for associating data with time information in the electronic device according to various embodiments of the present disclosure may further include receiving another data from another sensor and identifying third index information and another time information which correspond to the another data from the time information.

The method for associating data with time information in the electronic device according to various embodiments of the present disclosure may further include receiving image data from a camera included in the electronic device and identifying time information of the image data or time information of each frame of the image data.

The method for associating data with time information in the electronic device according to various embodiments of the present disclosure may further include identifying a first frame including time information corresponding to the third index information among at least one frames included in the image data and correcting a position in the image data in which the first frame is included at least based on information included in the another data.

The method for associating data with time information in the electronic device according to various embodiments of the present disclosure may further include identifying the time information through the application and identifying data corresponding to the application among plural data sensed by the sensor at least based on the identified time information.

The method for associating data with time information in the electronic device according to various embodiments of the present disclosure may further include stopping performing of an operation other than a preset operation and obtaining the time information, in which the notification signal may include an interrupt signal.

A method for associating data with time information in an electronic device including a sensor, a first processor, and a second processor according to various embodiments of the present disclosure includes sending a notification signal corresponding to data sensed using the sensor to the second processor by using the first processor, determining identification information corresponding to the data by using the first processor, and transmitting the data and the identification information corresponding to the data to the second processor by using the first processor.

The method for associating data with time information in an electronic device according to various embodiments of the present disclosure may further include receiving another data through the sensor, identifying time information corresponding to the notification signal, and to transmitting the another data and the time information to the second processor.

Figure 9A:
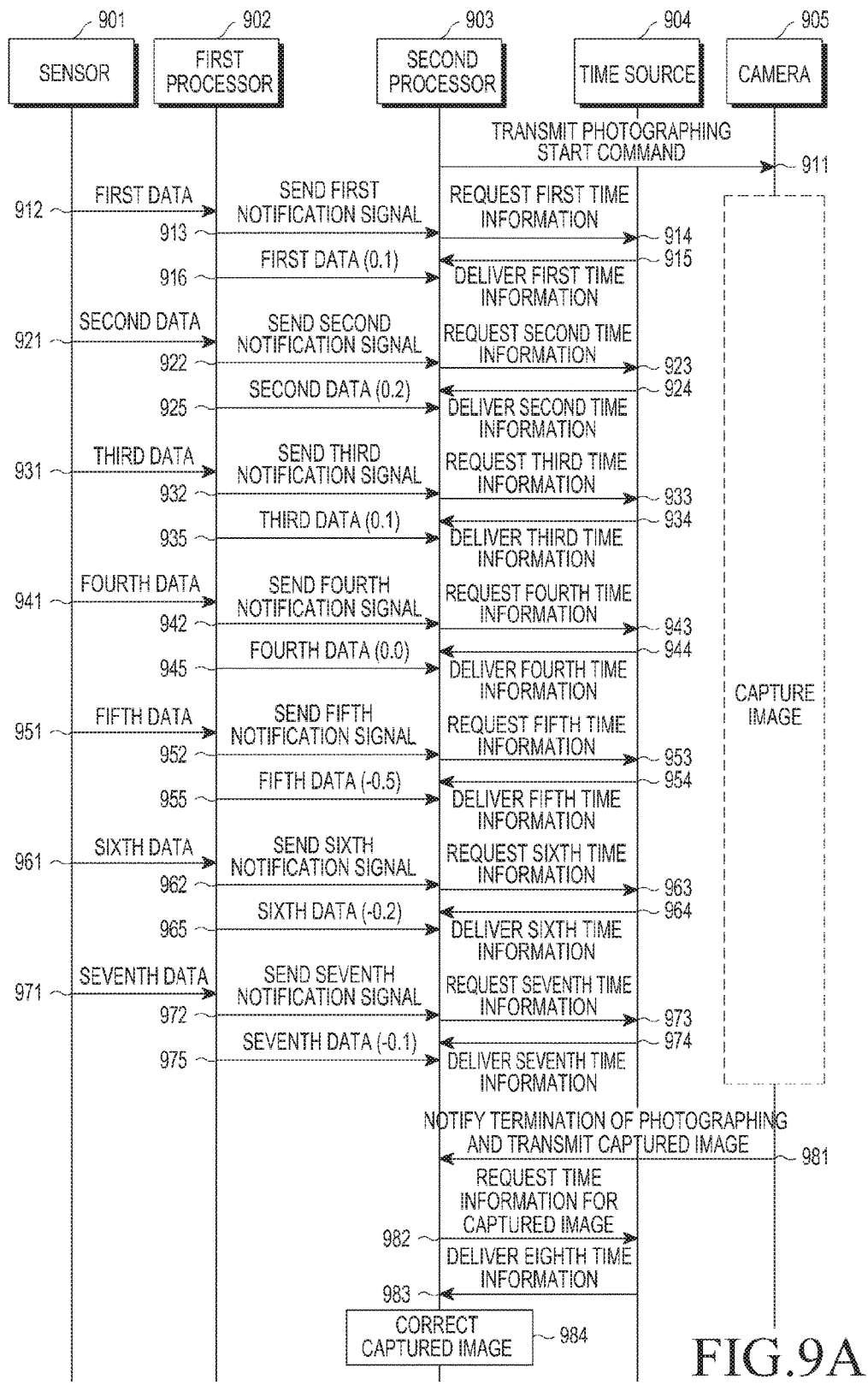
FIG. 9A illustrates a flowchart of operations between a sensor, processors, a time source, and an internal module to correct data obtained in the internal module based on sensor data according to various embodiments of the present disclosure.

FIG. 9A illustrates a flowchart of operations between a sensor, processors, a time source, and an internal module to correct data obtained in the internal module based on sensor data according to various embodiments of the present disclosure.

According to various embodiments of the present disclosure, an electronic device may include a sensor (e.g., an acceleration sensor or a gyro sensor) 901, a first processor 902, a second processor 903, a time source 904, and a camera 905, and when the second processor 903 performs a function of generating time information, the time source 904 may be omitted.

According to various embodiments of the present disclosure, an electronic device may identify gyro sensor data or acceleration sensor data sensed by the sensor, identify time information corresponding to respective data, and correct image data corresponding to the time information by a value of the respective data.

Referring to FIG. 9A, in operation 911, the second processor 903 transmits data instructing start of image capturing to the camera 905. For example, the command data may be transmitted to the camera 905 if reception of a preset input (e.g., selection of a button or execution of an application) is determined.

According to various embodiments of the present disclosure, the sensor 901 senses data corresponding to a rotational velocity during a unit time, and the sensed data responds to user's motion in a particular time. For example, the second processor 903 may identify data at a point in time corresponding to user's motion at the point in time from among data (e.g., a captured image) of an internal module (e.g., a camera), generated at the first point in time.

In operation 912, the sensor 901 transmits first data to the first processor 902.

In operation 913, the first processor 902 sends a first notification signal to the second processor 903, as the first data is received.

In operation 914, the second processor 903 sends a request for first time information for the first data to the time source 904.

In operation 915, the time source 904 generates the first time information for the first data and delivers the generated first time information to the second processor 903.

In operation 916, the first processor 902 transmits the received first data to the second processor 903. For example, a value of the first data is 0.1 (degree/sec), from which the value of the first data can be seen that shake by 0.1 degree for one second in a horizontal direction is sensed. For example, the first processor 902 may determine an index increment of first data to identify the index increment as time information of the first data.

In operation 921, the sensor 901 transmits second data to the first processor 902.

In operation 922, the first processor 902 sends a second notification signal to the second processor 903, as the second data is received.

In operation 923, the second processor 903 sends a request for second time information for the second data to the time source 904.

In operation 924, the time source 904 generates second time information for the second data and delivers the generated second time information to the second processor 903. For example, the second processor 903 may determine an index value counted from sending of the notification signal to reception of the second data as the second time information, and in this case, the above-described operation 923 or 924 may be omitted.

In operation 925, the first processor 902 transmits the received second data to the second processor 903. For example, a value of the second data is 0.2 (degree/sec), from which the value of the second data can be seen that shake by 0.2 degree for one second is sensed.

In operation 931, the sensor 901 transmits third data to the first processor 902.

In operation 932, the first processor 902 sends a third notification signal to the second processor 903, as the third data is received.

In operation 933, the second processor 903 sends a request for third time information for the third data to the time source 904.

In operation 934, the time source 904 generates the third time information for the third data and delivers the generated third time information to the second processor 903. For example, the second processor 903 may determine a sum of index values counted from sending of the notification signal to reception of the third data as the third time information, and in this case, the above-described operation 933 or 934 may be omitted.

In operation 935, the first processor 902 transmits the received third data to the second processor 903. For example, a value of the third data is 0.1 (degree/sec), from which the value of the third data can be seen that shake by 0.1 degree for one second is sensed.

In operation 941, the sensor 901 transmits fourth data to the first processor 902.

In operation 942, the first processor 902 sends a fourth notification signal to the second processor 903, as the fourth data is received.

In operation 943, the second processor 903 sends a request for fourth time information for the fourth data to the time source 904.

In operation 944, the time source 904 generates the fourth time information for the fourth data and delivers the generated fourth time information to the second processor 903. For example, the second processor 903 may determine a sum of index values counted from sending of the notification signal to reception of the fourth data as the fourth time information, and in this case, the above-described operation 943 or 944 may be omitted.

In operation 945, the first processor 902 transmits the received fourth data to the second processor 903. For example, a value of the fourth data is 0.0 (degree/sec), from which the value of the fourth data can be seen that shake by 0 degree for one second is sensed.

In operation 951, the sensor 901 transmits fifth data to the first processor 902.

In operation 952, the first processor 902 sends a fifth notification signal to the second processor 903, as the fifth data is received.

In operation 953, the second processor 903 sends a request for fifth time information for the fifth data to the time source 904.

In operation 954, the time source 904 generates the fifth time information for the fifth data and delivers the generated fifth time information to the second processor 903. For example, the second processor 903 may determine a sum of index values counted from sending of the notification signal to reception of the fifth data as the fifth time information, and in this case, the above-described operation 953 or 954 may be omitted.

In operation 955, the first processor 902 transmits the received fifth data to the second processor 903. For example, a value of the fourth data is −0.1 (degree/sec), from which the value of the fourth data can be seen that movement by −0.1 degree for one second is sensed.

In operation 961, the sensor 901 transmits sixth data to the first processor 902.

In operation 962, the first processor 902 sends a sixth notification signal to the second processor 903, as the sixth data is received.

In operation 963, the second processor 903 sends a request for sixth time information for the sixth data to the time source 904.

In operation 964, the time source 904 generates the sixth time information for the sixth data and delivers the generated sixth time information to the second processor 903. For example, the second processor 903 may determine a sum of index values counted from sending of the notification signal to reception of the sixth data as the sixth time information, and in this case, the above-described operation 963 or 964 may be omitted.

In operation 965, the first processor 902 transmits the received sixth data to the second processor 903. For example, a value of the sixth data is −0.2 (degree/sec), from which the value of the sixth data can be seen that movement by −0.2 degree for one second is sensed.

In operation 971, the sensor 901 transmits seventh data to the first processor 902.

In operation 972, the first processor 902 sends a seventh notification signal to the second processor 903, as the seventh data is received.

In operation 973, the second processor 903 sends a request for seventh time information for the seventh data to the time source 904.

In operation 974, the time source 904 generates the seventh time information for the seventh data and delivers the generated seventh time information to the second processor 903. For example, the second processor 903 may determine a sum of index values counted from sending of the notification signal to reception of the seventh data as the seventh time information, and in this case, the above-described operation 973 or 974 may be omitted.

In operation 975, the first processor 902 transmits the received seventh data to the second processor 903. For example, a value of the seventh data is −0.1 (degree/sec), from which the value of the seventh data can be seen that movement by −0.1 degree for one second is sensed.

According to various embodiments of the present disclosure, the first processor 902 determines an index increment from sending of a notification signal to transmission of data (e.g., the first through seventh data) of the sensor 901. For example, data transmitted to the second processor 903 may be transmitted including the index increment.

According to various embodiments of the present disclosure, upon receiving data of the sensor 901, the second processor 903 matches time information with the data and stores the time information together with the data. For example, time information corresponding to each data may correspond to an index value increased from a point in time indicated by particular time information up to a point in time in which the data is received.

In operation 981, the camera 905 notifies the second processor 903 of termination of photographing and transmits a captured image. For example, the captured image may have been captured based on a result of operation 911.

In operation 982, the second processor 903 sends a request for eighth time information for the captured image to a time source 904.

According to various embodiments of the present disclosure, the eighth time information may include an index count value from time information generated as a photographing start command is transmitted, or may correspond to time information requested as a photographing termination notification is received.

In operation 983, the time source 904 generates the eighth time information for the captured image and delivers the generated eighth time information to the second processor 903. For example, the eighth time information may indicate a point in time in which the captured image is received by the second processor 903.

According to various embodiments of the present disclosure, the second processor 903 may determine a point in time indicated by the eighth time information and compare the determined point in time with a point in time in which each horizontal frame of the captured image in the point in time is captured.

According to various embodiments of the present disclosure, each frame may include a point in which in which the frame is captured and a motion angle value of the frame. For example, the camera 905 may sense a motion angle value (e.g., 0°) of a particular captured frame (e.g., a first frame 981) with respect to a position at a point in time in which a photographing start command is received.

According to various embodiments of the present disclosure, the camera 905 captures a horizontal or vertical frame in a predetermined order and obtains the captured image including captured frames. For example, as each frame is captured in a situation where an electronic device moves (e.g., a hand shake, a user situated in a moving vehicle, etc.), the frame may be captured in a position moved from a particular position due to movement of the electronic device.

In operation 984, the second processor 903 corrects the captured image. For example, the second processor 903 may identify data of the sensor 901 including time information corresponding to a point in time in which each frame is captured, and move the frame by data corresponding to the frame in a position to which the frame is moved.

According to various embodiments of the present disclosure, the second processor 903 identifies data of the sensor 901 corresponding to each frame, based on the eighth time information. For example, the data of the sensor 901 corresponding to the eighth time information may correspond to data in which an index for a notification signal is increased corresponding to an index increment of the eighth time information or data including time information indicating a point in time corresponding to a point in time of the eighth time information.

According to various embodiments of the present disclosure, the second processor 903 executes at least one application (e.g., a camera application) based on a user input or a particular situation. Once the application is executed, the second processor 903 sends a photographing start command 911 to the camera 905 based on the user input. The camera 905 obtains an image frame-by-frame based on the photographing start command of the second processor 903.

According to various embodiments of the present disclosure, the camera 905 delivers a frame associated with an image to the second processor 903. The second processor 903 obtains time information by using the time source 904, and associates a frame received from the camera 905 with the obtained time information. For example, until the photographing termination notification is determined after the photographing start command is determined, the camera 905 delivers obtained each frame to the second processor 903 which then obtains time information every time when receiving each frame from the camera 905 and associates the frame with the time information. The second processor 903 compares sensor data including time information with a frame including the time information to correct an image including the frame.

Figure 9B:
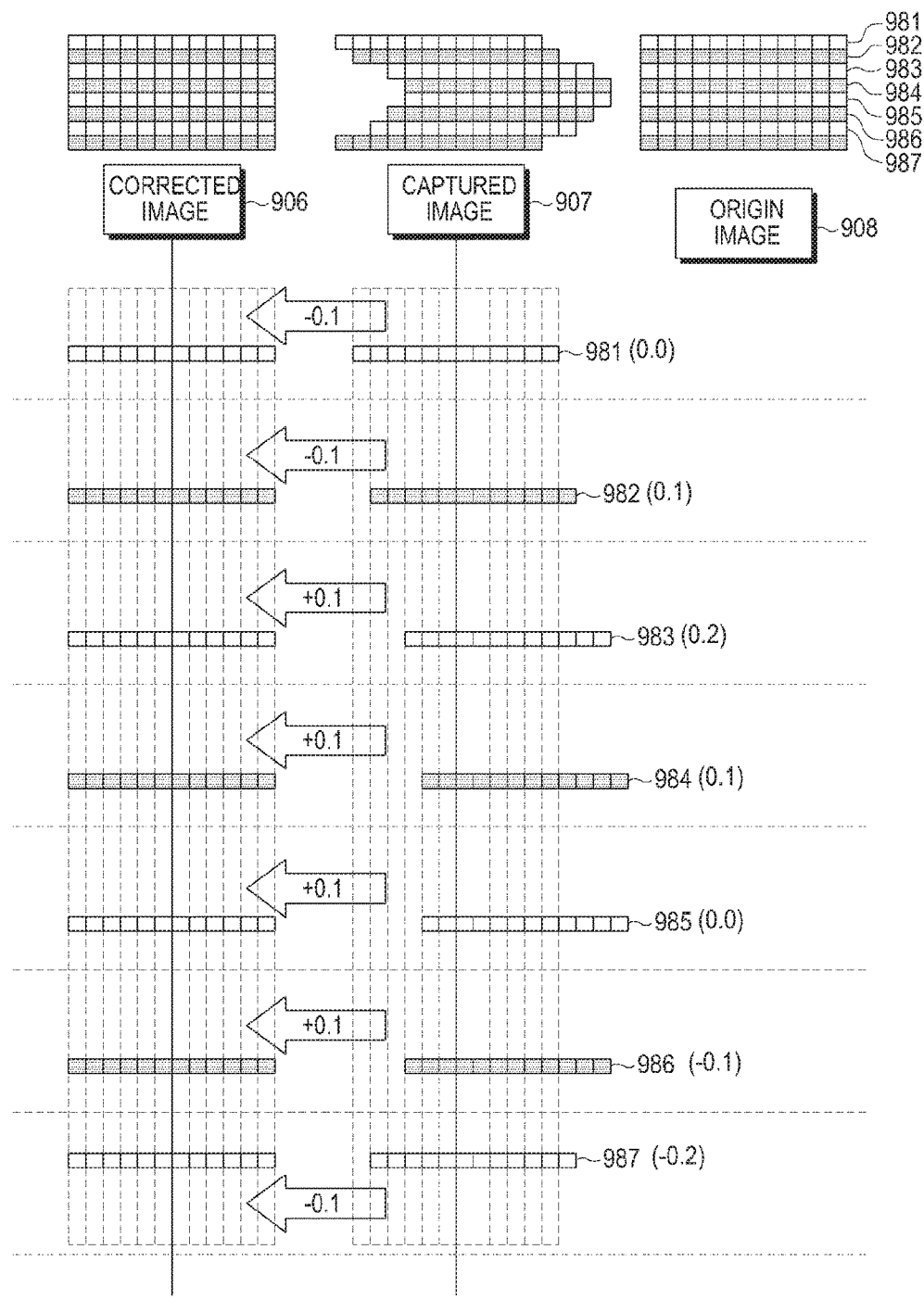
FIG. 9B illustrates an example of a result of correcting data obtained in an internal module based on sensor data according to various embodiments of the present disclosure.

FIG. 9B illustrates an example of a result of correcting data obtained in an internal module based on sensor data according to various embodiments of the present disclosure.

Referring to FIG. 9B, an electronic device identifies a corrected image 906 moved for each frame from a captured image 907, and the corrected image 906 corresponds to an original image 908 captured in a situation where the electronic device does not move.

According to various embodiments of the present disclosure, the captured image 907 may include at least one frame (e.g., first through seventh frames 981 through 987). The at least one frame may be divided horizontally or vertically, and may have been captured sequentially from a frame located up or to the left in a specific order.

According to various embodiments of the present disclosure, in the captured image 907, a first frame 981 may be captured in a position moved, from a position corresponding to a photographing start point in time in the unit of an angle per unit time (degree/sec), by 0.0, a second frame 982 by 0.1, a third frame 983 by 0.2, a fourth frame 984 by 0.1, a fifth frame 985 by 0.0, a sixth frame 986 by −0.1, and a seventh frame 987 by −0.2.

According to various embodiments of the present disclosure, the sensor 901 senses, as a value in the unit of an angle per unit time (degree/sec), first data as 0.1, second data as 0.2, third data as 0.1, fourth data as 0.0, fifth data as −0.1, sixth data as −0.2, and seventh data as −0.1.

According to various embodiments of the present disclosure, an index increment for a notification signal for data of the sensor 901 may correspond to an index increment of time information generated as completion of capturing of the captured image 907.

According to various embodiments of the present disclosure, the processor 903 identifies data of the sensor 901 corresponding to a frame of the captured image 907 and moves the frame in an opposite direction from a position to which the frame is moved, by a value of the identified data corresponding to the frame, thereby correcting the position in which the frame is captured.

For example, the first frame 981 moved by 0.0 may be moved by the value of the first data (0.1) in the opposite direction, thus being moved by −0.1 with respect to the captured image 907. The second frame 982 moved by 0.1 may be moved by the value of the second data (0.2) in the opposite direction, thus being moved by −0.1 from a position where the first frame 981 is captured. The third frame 983 moved by 0.2 may be moved by the value of the third data (0.1) in the opposite direction, thus being moved by 0.1 from a position where the second frame 982 is captured. The fourth frame 984 moved by 0.1 may be moved by the value of the fourth data (0.0) in the opposite direction, thus being moved by 0.1 from a position where the third frame 983 is captured. The fifth frame 985 moved by 0.0 may be moved by the value of the fifth data (−0.1) in the opposite direction, thus being moved by 0.1 from a position where the fourth frame 984 is captured. The sixth frame 986 moved by −0.1 may be moved by the value of the sixth data (−0.2) in the opposite direction, thus being moved by 0.1 from a position where the fifth frame 985 is captured. The seventh frame 987 moved by 0.2 may be moved by the value of the seventh data (−0.1) in the opposite direction, thus being moved by −0.1 from a position where the sixth frame 986 is captured. The eighth frame 988 moved by 0.0 may be moved by the value of the eighth data (e.g., +0.1) in the opposite direction, thus being moved by +0.1 from a position where the seventh frame 987 is captured.

Figure 10:
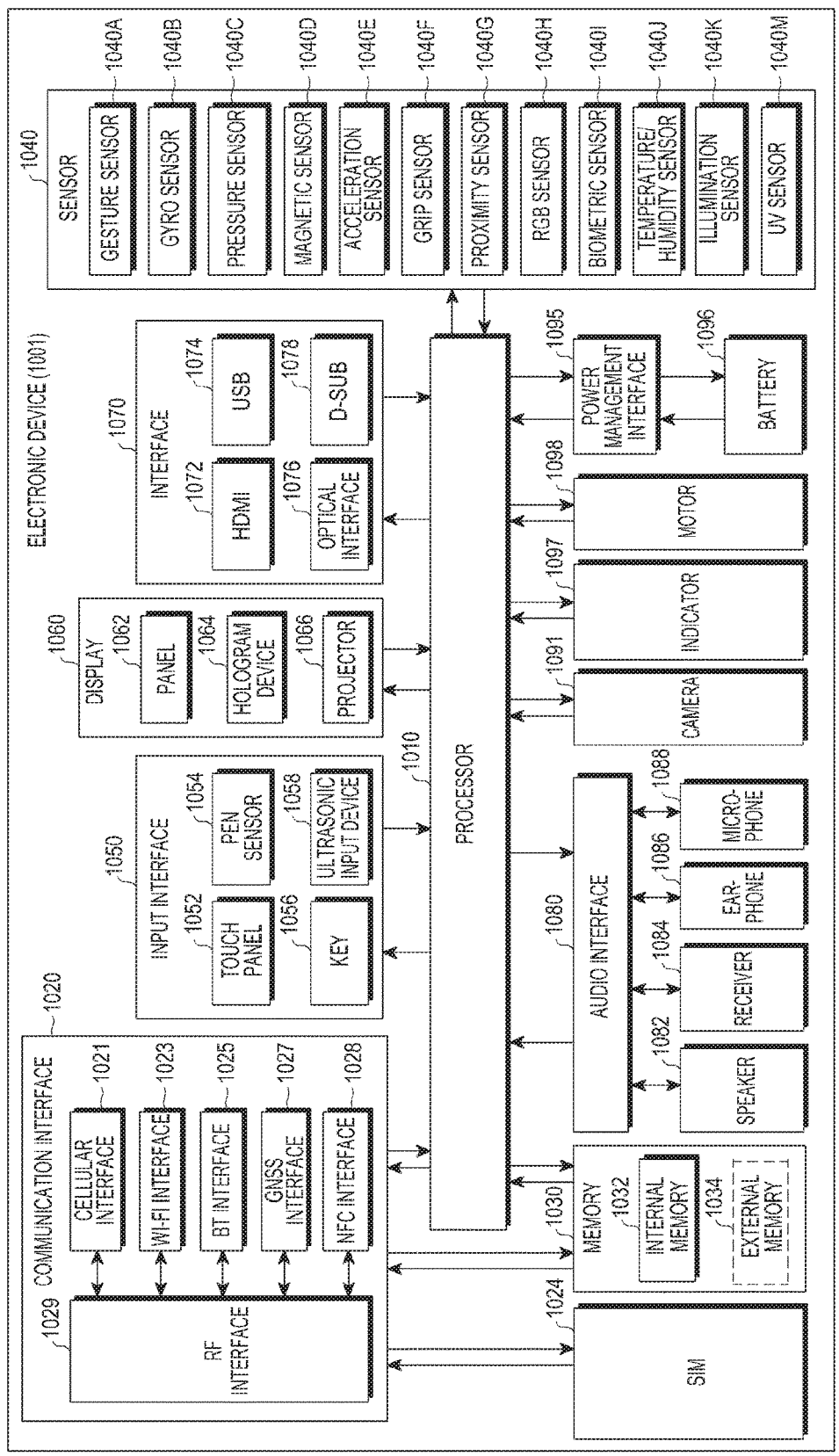
FIG. 10 illustrates a block diagram of an electronic device according to various embodiments of the present disclosure.

FIG. 10 illustrates a block diagram of an electronic device according to various embodiments of the present disclosure.

Referring to FIG. 10, the electronic device 1001 may include the entire electronic device 101 illustrated in FIG. 1 or a part thereof. The electronic device 1001 may include one or more processors (e.g., application processors (APs)) 1010, a communication interface 1020, a subscriber identification module (SIM) 1022, a memory 1030, a sensor 1040, an input interface 1050, a display 1060, an interface 1070, an audio interface 1080, a camera 1091, a power management interface 1095, a battery 1096, an indicator 1097, and a motor 1098.

The processor 1010 controls multiple hardware or software components connected to the processor 1010 by driving an operating system (OS) or an application program, and performs processing and operations with respect to various data. The processor 1010 may be implemented with, for example, a system on chip (SoC). According to an embodiment, the processor 1010 may further include a graphic processing unit (GPU) and/or an image signal processor. The processor 1010 may include at least some of the elements illustrated in FIG. 10 (e.g., the cellular interface 1021). The processor 1010 loads a command or data received from at least one of other elements (e.g., a non-volatile memory) into a volatile memory to process the command or data, and stores various data in the non-volatile memory.

The communication interface 1020 may have a configuration that is the same as or similar to the communication interface 170 illustrated in FIG. 1. The communication interface 1020 may include, for example, at least one of the cellular interface 1021, a WiFi interface 1023, a Bluetooth (BT) interface 1025, a GNSS interface 1027 (e.g., a GPS interface, a Glonass interface, a Beidou interface, or a Galileo interface), a near field communication (NFC) interface 1028, and a radio frequency (RF) interface 1029.

The cellular interface 1021 may provide, for example, a voice call, a video call, a text service, or an Internet service over a communication network. According to an embodiment, the cellular interface 1021 identifies and authenticates the electronic device 1001 in a communication network by using the SIM 1022 (e.g., a SIM card). According to an embodiment, the cellular interface 1021 performs at least one of functions that may be provided by the processor 1010. According to an embodiment, the cellular interface 1021 may include a communication processor (CP).

Each of the WiFi interface 1023, the BT interface 1025, the GNSS interface 1027, and the NFC interface 1028 may include, for example, a processor for processing data transmitted and received by a corresponding interface. According to some embodiment, at least some (e.g., two or more) of the cellular interface 1021, the WiFi interface 1023, the BT interface 1025, the GNSS interface 1027, and the NFC interface 1028 may be included in one integrated chip (IC) or IC package.

The RF interface 1029 may, for example, transmit and receive a communication signal (e.g., an RF signal). The RF interface 1029 may include a transceiver, a power amp module (PAM), a frequency filter, a low noise amplifier (LNA), or an antenna. According to another embodiment, at least one of the cellular interface 1021, the WiFi interface 1023, the BT interface 1025, the GNSS interface 1027, and the NFC interface 1028 may transmit and receive an RF signal through the separate RF interface.

The SIM 1022 may, for example, include a card including an SIM and/or an embedded SIM, and may include unique identification information (e.g., an integrated circuit card identifier (ICCID) or subscriber information (e.g., an international mobile subscriber identity (IMSI)).

The memory 1030 (e.g., the memory 130) may, for example, include an internal memory 1032 and/or an external memory 1034. The internal memory 1032 may, for example, include at least one of a volatile memory (e.g., dynamic random access memory (DRAM), static RAM (SRAM), synchronous dynamic RAM (SDRAM), etc.), and a non-volatile memory (e.g., one time programmable read only memory (OTPROM), programmable ROM (PROM), erasable and programmable ROM (EPROM), electrically erasable and programmable ROM (EEPROM), etc.), mask ROM, flash ROM, NAND flash memory, NOR flash memory, etc.), and a solid state drive (SSD).

The external memory 1034 may further include flash drive, for example, compact flash (CF), secure digital (SD), micro-SD, mini-SD, extreme Digital (xD), a multi-media card (MMC), or a memory stick. The external memory 1034 may be functionally and/or physically connected with the electronic device 1001 through various interfaces.

The sensor 1040 measures physical quantity or senses an operation state of the electronic device 1001 to convert the measured or sensed information into an electric signal. The sensor 1040 may, for example, include at least one of a gesture sensor 1040A, a gyro sensor 1040B, a pressure sensor 1040C, a magnetic sensor 1040D, an acceleration sensor 1040E, a grip sensor 1040F, a proximity sensor 1040G, a color sensor 1040H (e.g., RGB sensor), a biometric sensor 1040I, a temperature/humidity sensor 1040J, an illumination sensor 1040K, a ultraviolet (UV) sensor 1040L, and a touch sensor 1040M. Additionally or alternatively, the sensor 1040 may include an E-nose sensor (not shown), an electromyography (EMG) sensor (not shown), an electroencephalogram (EEG) sensor (not shown), an electrocardiogram (ECG) sensor (not shown), an infrared (IR) sensor, an iris sensor, and/or a fingerprint sensor. The sensor 1040 may further include a control circuit for controlling at least one sensor included therein. In some embodiment, the electronic device 1001 may further include a processor configured to control the sensor 1040 as part of or separately from the processor 1010, to control the sensor 1040 during a sleep state of the processor 1010.

The input interface 1050 may include, for example, a touch panel 1052, a (digital) pen sensor 1054, a key 1056, or an ultrasonic input device 1058. The touch panel 1052 may use at least one of a capacitive type, a resistive type, an IR type, or an ultrasonic type. The touch panel 1052 may further include a control circuit. The touch panel 1052 may further include a tactile layer to provide tactile reaction to the user. According to an embodiment, the touch panel 1052 may include a pressure sensor (or a "force sensor", interchangeably used hereinafter) capable of measuring a strength of a pressure by a user's touch. The pressure sensor may be implemented integrally with the touch panel 1052 or may be implemented as one or more sensors separate from the touch panel 1052.

The (digital) pen sensor 1054 may include a recognition sheet which is a part of the touch panel 252 or a separate recognition sheet. The key 1056 may also include a physical button, an optical key, or a keypad. The ultrasonic input device 1058 senses ultrasonic waves generated by an input means through a microphone (e.g., the microphone 1088) and checks data corresponding to the sensed ultrasonic waves. The display 1060 (e.g., the display 160) may include a panel 1062, a hologram device 1064, or a projector 1066. The panel 1062 may have a configuration that is the same as or similar to the display 160 illustrated in FIG. 1. The panel 1062 may be implemented to be flexible, transparent, or wearable. The panel 1062 may be configured with the touch panel 1052 in one module. The hologram device 1064 shows a stereoscopic image in the air by using interference of light. The projector 1066 displays an image onto an external screen through projection of light. The screen may be positioned inside or outside the electronic device 1001. According to an embodiment, the display 1060 may further include a control circuit for controlling the panel 1062, the hologram device 1064, or the projector 1066.

According to an embodiment, the interface 1070 may include a high-definition multimedia interface (HDMI) 1072, a universal serial bus (USB) 1074, an optical communication 1076, or a D-subminiature 1078. The interface 1070 may be included in the communication interface 170 illustrated in FIG. 1. Additionally or alternatively, the interface 1070 may include a mobile high-definition link (MHL) interface, an SD/multi-media card (MMC) interface, or an Infrared Data Association (IrDA) interface.

The audio interface 1080 bi-directionally converts sound and an electric signal. At least one element of the audio interface 1080 may be included in the I/O interface 145 illustrated in FIG. 1. The audio interface 1080 processes sound information input or output through a speaker 1087, a receiver 1084, an earphone 1086, or a microphone 1088.

The camera 1091 is, for example, a device capable of capturing a still image or a moving image, and according to an embodiment, may include one or more image sensors (e.g., a front sensor or a rear sensor), a lens, an image signal processor (ISP), or a flash (e.g., an LED, a xenon lamp, etc.).

The power management interface 1095 manages power of the electronic device 1001. According to an embodiment, the power management interface 1095 may include a power management integrated circuit (PMIC), a charger IC, or a battery fuel gauge. The PMIC may have a wired and/or wireless charging scheme. The wireless charging scheme includes a magnetic-resonance type, a magnetic induction type, and an electromagnetic type, and for wireless charging, an additional circuit, for example, a coil loop, a resonance circuit, or a rectifier may be further included. The battery gauge measures the remaining capacity of the battery 1096 or the voltage, current, or temperature of the battery 296 during charging. The battery 1096 may include a rechargeable battery and/or a solar battery.

The indicator 1097 displays a particular state, for example, a booting state, a message state, or a charging state, of the electronic device 1001 or a part thereof (e.g., the processor 1010). The motor 1098 converts an electric signal into mechanical vibration or generates vibration or a haptic effect. Although not shown, the electronic device 1001 may include a processing device (e.g., a GPU) for supporting a mobile TV. The processing device for supporting the mobile TV processes media data according to, a standard such as digital multimedia broadcasting (DMB), digital video broadcasting (DVB), or mediaFlo™.

Each of the foregoing elements described herein may be configured with one or more components, names of which may vary with a type of the electronic device.

In various embodiments of the present disclosure, the electronic device may include at least one of the foregoing elements, some of which may be omitted or to which other elements may be added. In addition, some of the elements of the electronic device according to various embodiments of the present disclosure may be integrated into one entity to perform functions of the corresponding elements in the same manner as before they are integrated.

Figure 11:
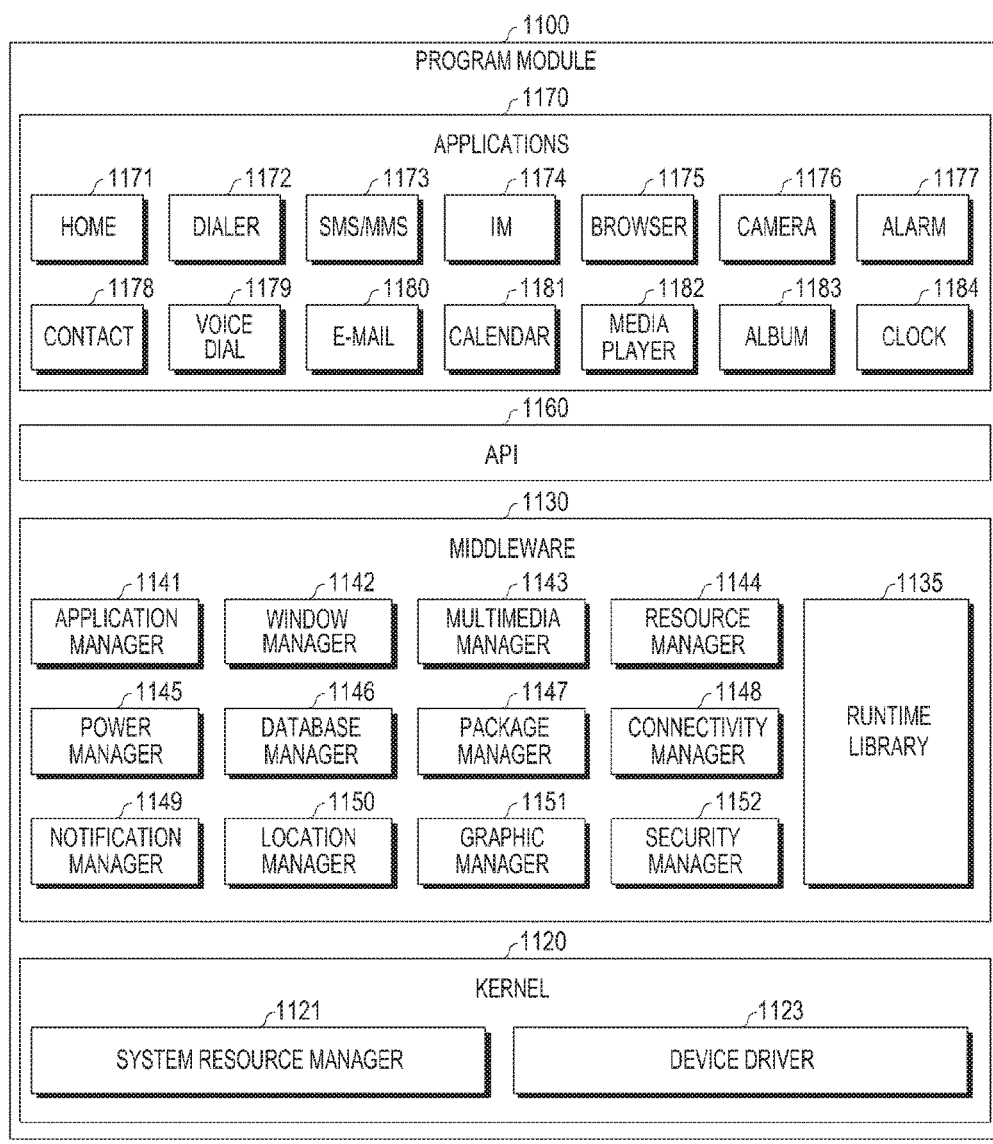
FIG. 11 illustrates a block diagram of a program module according to various embodiments of the present disclosure.

FIG. 11 illustrates a block diagram of a program module according to various embodiments of the present disclosure.

According to an embodiment, a programming module 1110 (e.g., the program 140) may include an OS for controlling resources associated with an electronic device (e.g., the electronic device 101) and/or various applications (e.g., the application program 147) executed on the OS.

The OS may include Android, iOS, Windows, Symbian, Tizen, or Bada.

The programming module 1110 may include, for example, a kernel 1120, middleware 1130, an application programming interface (API) 1160, and/or an application 1170. At least a part of the programming module 1110 may be preloaded on an electronic device or may be downloaded from an external device (e.g., the first electronic device 102, the second electronic device 104, or the server 106).

The kernel 1120 (e.g., the kernel 141) may, for example, include a system resource manager 1121 and/or a device driver 1123. The system resource manager 1121 may perform control, allocation, retrieval of system resources, and so forth. According to an embodiment, the system resource manager 1121 may include a process management unit, a memory management unit, or a file system. The device driver 1123 may include, for example, a display driver, a camera driver, a Bluetooth driver, a shared memory driver, a USB driver, a keypad driver, a WiFi driver, an audio driver, or an inter-process communication (IPC) driver.

The middleware 1130 may include provide functions that the application 1170 commonly requires or provide various functions to the application 1170 through the API 1160 to allow the application 1170 to efficiently use a limited system resource in an electronic device. According to an embodiment, the middleware 1130 (e.g., the middleware 143) may include at least one of a runtime library 1135, an application manager 1141, a window manager 1142, a multimedia manager 1143, a resource manager 1144, a power manager 1145, a database manager 1146, a package manager 1147, a connectivity manager 1148, a notification manager 1149, a location manager 1150, a graphic manager 1151, and a security manager 1152.

The runtime library 1135 may include a library module that a compiler uses to add a new function through a programming language while the application 1170 is executed. The runtime library 1135 performs functions relating to an input/output, memory management, or calculation operation.

The application manager 1141 manages a life cycle of at least one application among the applications 1170. The window manager 1142 manages a GUI resource using a screen. The multimedia manager 1143 recognizes a format necessary for playing various media files and performs encoding or decoding on a media file by using a codec appropriate for a corresponding format. The resource manager 1144 manages a resource such as source code, memory, or storage space of at least one application among the applications 1170.

The power manager 1145 manages a battery or power, for example, in operation with a basic input/output system (BIOS) and provides power information necessary for an operation of the electronic device. The database manager 1146 performs a management operation to generate, search or change a database used for at least one application among the applications 1170. The package manager 1147 manages the installation or update of an application distributed in a package file format.

The connectivity manager 1148 manages a wireless connection such as a WiFi or Bluetooth connection. The notification manager 1149 displays or notifies events such as arrival messages, appointments, and proximity alerts in a manner that is not disruptive to a user. The location manager 1150 manages location information of an electronic device. The graphic manager 1151 manages a graphic effect to be provided to a user or a user interface relating thereto. The security manager 1152 provides a general security function necessary for system security or user authentication. According to an embodiment, if the electronic device (e.g., the electronic device 101) has a call function, the middleware 1130 may further include a telephony manager for managing a voice or video call function of the electronic device.

The middleware 1130 may include a middleware module forming a combination of various functions of the above-mentioned internal elements. The middleware 1130 may provide modules specified according to types of OS so as to provide distinctive functions. Additionally, the middleware 1130 may delete some of existing elements or add new elements dynamically.

The API 1160 (e.g., the API 145) may be provided as a set of API programming functions with a different configuration according to the OS. In the case of Android or iOS, for example, one API set may be provided by each platform, and in the case of Tizen, two or more API sets may be provided.

The application 1170 (e.g., the application program 147) may include one or more applications capable of providing a function, for example, a home application 1171, a dialer application 1172, a short messaging service/multimedia messaging service (SMS/MMS) application 1173, an instant message (IM) application 1174, a browser application 1175, a camera application 1176, an alarm application 1177, a contact application 1178, a voice dial application 1179, an e-mail application 1180, a calendar application 1181, a media player application 1182, an album application 1183, a clock application 1184, a health care application (e.g., an application for measuring an exercise amount, a blood sugar, etc.), or an environment information providing application (e.g., an application for providing air pressure, humidity, or temperature information or the like).

According to an embodiment, the application 1170 may include an application (hereinafter, an "information exchange application" for convenience) supporting information exchange between the electronic device (e.g., the electronic device 101) and an external electronic device (e.g., the electronic device 102 or 104). The information exchange application may include, for example, a notification relay application for transferring specific information to the external electronic device or a device management application for managing the external electronic device.

For example, the notification relay application may include a function for transferring notification information generated in another application (e.g., an SMS/MMS application, an e-mail application, a health care application, or an environment information application) of the electronic device to an external electronic device (e.g., the first electronic device 102 or the second electronic device 104). The notification relay application may receive notification information from an external electronic device to provide the same to a user.

The device management application may manage (e.g., install, remove, or update) at least one function (e.g., turn on/turn off of an external electronic device itself (or a part thereof) or control of brightness (or resolution) of a display) of an external device (e.g., the first electronic device 102 or the second electronic device 104) communicating with the electronic device, a service provided by an application operating in an external electronic device or provided by the external electronic device (e.g., a call service or a message service).

According to an embodiment, the application 37 may include an application (e.g., device health care application of mobile medical equipment) designated according to an attribute of the external electronic device (e.g., the first electronic device 102 or the second electronic device 104). According to an embodiment, the application 1170 may include an application received from the external electronic device (e.g., the server 106, the first electronic device 102, or the second electronic device 104). According to an embodiment, the application 1170 may include a preloaded application or a third party application that may be downloaded from the server. Names of elements of the programming module 1110 according to the illustrated embodiment may vary depending on a type of an OS.

According to various embodiments, at least a part of the programming module 1110 may be implemented by software, firmware, hardware, or a combination of at least two of them. The at least a part of the programming module 1110 may be implemented (e.g., executed) by a processor (e.g., the processor 1010). The at least a part of the programming module 1110 may include, for example, modules, programs, routines, sets of instructions, or processes for performing one or more functions.

A term "module" used herein may mean, for example, a unit including one of or a combination of two or more of hardware, software, and firmware. The "module" may be interchangeably used with a unit, a logic, a logical block, a component, or a circuit. The "module" may be a minimum unit or a portion of an integrated component. The "module" may be a minimum unit or a portion thereof performing one or more functions. The "module" may be implemented mechanically or electronically. For example, the "module" according to the embodiments may include at least one of an application-specific integrated circuit (ASIC) chip, field-programmable gate arrays (FPGAs), and a programmable-logic device performing certain operations already known or to be developed.

At least a part of an apparatus (e.g., modules or functions thereof) or a method (e.g., operations) according to various embodiments of the present disclosure may be implemented with a command stored in a computer-readable storage medium in the form of a programming module. When the instructions are executed by one or more processors (for example, the processor 120), the one or more processors may perform functions corresponding to the instructions. The computer-readable storage medium may be, for example, a memory included in the memory 130.

According to various embodiments of the present disclosure, provided is a storage medium (e.g., the memory 130) having stored therein instructions which, when executed by at least one processor, cause the at least one processor to perform at least one operation, the at least one operation including receiving a notification signal corresponding to data sensed using the sensor from a first processor, determining time information and first identification information that correspond to the notification signal by using a second processor in response to the reception, receiving the data and second identification information corresponding to the notification signal from the first processor, associating the data with the time information at least based on the first identification information and the second identification information, and providing the data associated with the time information to an application by using the second processor.

The computer readable recording medium includes hard disk, floppy disk, or magnetic media (e.g., a magnetic tape, optical media (e.g., compact disc read only memory (CD-ROM) or digital versatile disc (DVD), magneto-optical media (e.g., floptical disk), a hardware device (e.g., ROM, RAM, flash memory, etc.), and so forth. Further, the program instructions include a machine language code created by a complier and a high-level language code executable by a computer using an interpreter. The foregoing hardware device may be configured to be operated as at least one software module to perform an operation of the present disclosure, or vice versa.

Modules or programming modules according to various embodiments of the present disclosure may include one or more of the foregoing elements, have some of the foregoing elements omitted, or further include additional other elements.

Operations performed by the modules, the programming modules or other elements may be executed in a sequential, parallel, repetitive or heuristic manner. Also, some of the operations may be executed in different order or omitted, or may have additional different operations.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. An electronic device, implemented in home-appliances system, comprising:
   a sensor;
   a first processor configured to obtain data sensed using the sensor; and
   a second processor configured to execute an application, wherein the second processor is further configured to:
   receive a notification signal corresponding to the data from the first processor;
   determine time information that corresponds to a time when the notification signal is received and first identification information that corresponds to first number of times that the notification signal is received;
   receive the data and second identification information that corresponds to second number of times that the notification signal is sent from the first processor;
   associate the data with the time information according to whether the first identification information corresponds to the second identification information; and
   provide the data associated with the time information to the application if the first identification information corresponds to the second identification information.

2. The electronic device of claim 1, further comprising a non-transitory memory, wherein the second processor is configured to:
   determine the first identification information as identification information corresponding to the second identification information; and
   associate the data with the time information based on a result of the determination; and
   store the data and the time information in the non-transitory memory.

3. The electronic device of claim 1, wherein the second processor is further configured to:
   generate first index information corresponding to the notification signal; and
   generate second index information based on the first index information in response to reception of another notification signal.

4. The electronic device of claim 1, further comprising another sensor configured to sense first data related to the electronic device, wherein the second processor is further configured to:
   receive the first data from the other sensor; and
   determine index information and first time information corresponding to the first data based on in part of the time information.

5. The electronic device of claim 4, further comprising a camera, wherein the second processor is further configured to:
   receive image data from the camera included in the electronic device; and
   identify at least one of time information of the image data or time information of each frame of the image data.

6. The electronic device of claim 5, wherein the second processor is further configured to:
   identify a first frame comprising time information corresponding to third index information among at least one frame included in the image data; and
   correct a position comprising the first frame in the image data based on information included in the other data.

7. The electronic device of claim 1, wherein the second processor is further configured to identify data corresponding to the application from data sensed by the sensor based on the determined time information.

8. The electronic device of claim 1, wherein the notification signal comprises an interrupt signal.

9. A method for associating data with time information in an electronic device, implemented in home-appliances system, comprising a sensor, a first processor, and a second processor, the method comprising:
   receiving a notification signal corresponding to data sensed using the sensor from the first processor;
   determining, by the second processor, the time information that corresponds to a time when the notification signal is received and first identification information that corresponds to first number of times that the notification signal is received;

receiving the data and second identification information that corresponds to second number of times that the notification signal is sent from the first processor;

associating the data with the time information according to whether the first identification information corresponds to the second identification information, by the second processor; and providing the data associated with the time information to an application if the first identification information corresponds to the second identification information, by using the second processor.

10. The method of claim 9, further comprising:

determining the first identification information as identification information corresponding to the second identification information; and associating the data with the time information based on a result of the determination; and storing the data and the time information in a non-transitory memory.

11. The method of claim 9, further comprising:

generating first index information as identification information corresponding to the second identification information; and generating second index information based on the first index information in response to reception of another notification signal.

12. The method of claim 9, further comprising:

receiving first data from another sensor; and determining index information and first time information corresponding to the first data based on in part of the time information.

13. The method of claim 12, further comprising:

receiving image data from a camera included in the electronic device; and identifying at least one of time information of the image data or time information of each frame of the image data.

14. The method of claim 13, further comprising:

identifying a first frame comprising time information corresponding to third index information among at least one frame included in the image data; and correcting a position comprising the first frame in the image data based on information included in the other data.

15. The method of claim 9, further comprising identifying data corresponding to the application from data sensed by the sensor based on a result of the determined time information.

16. The method of claim 9, wherein the notification signal comprises an interrupt signal.

* * * * *